US008399645B2

(12) United States Patent
Campana et al.

(10) Patent No.: US 8,399,645 B2
(45) Date of Patent: Mar. 19, 2013

(54) CHIMERIC RECEPTORS WITH 4-1BB STIMULATORY SIGNALING DOMAIN

(75) Inventors: Dario Campana, Germantown, TN (US); Chihaya Imai, Niigata (JP)

(73) Assignee: St. Jude Children's Research Hospital, Inc., Memphis, TN (US)

( * ) Notice: Subject to any disclaimer, the term of this patent is extended or adjusted under 35 U.S.C. 154(b) by 0 days.

(21) Appl. No.: 13/548,148

(22) Filed: Jul. 12, 2012

(65) Prior Publication Data

US 2012/0282256 A1  Nov. 8, 2012

Related U.S. Application Data

(63) Continuation of application No. 13/244,981, filed on Sep. 26, 2011, now abandoned, which is a continuation of application No. 12/206,204, filed on Sep. 8, 2008, now Pat. No. 8,026,097, which is a continuation of application No. 11/074,525, filed on Mar. 8, 2005, now Pat. No. 7,435,596, which is a continuation-in-part of application No. 10/981,352, filed on Nov. 4, 2004, now abandoned.

(60) Provisional application No. 60/517,507, filed on Nov. 5, 2003.

(51) Int. Cl.
*C07H 21/04* (2006.01)
*C12N 15/00* (2006.01)
(52) U.S. Cl. ............... 536/23.4; 435/320.1; 435/455
(58) Field of Classification Search .................. None
See application file for complete search history.

(56) References Cited

U.S. PATENT DOCUMENTS

| | | | |
|---|---|---|---|
| 5,359,046 A | 10/1994 | Capon et al. | |
| 5,674,704 A | 10/1997 | Goodwin et al. | |
| 5,686,281 A | 11/1997 | Roberts | |
| 6,103,521 A | 8/2000 | Capon et al. | |
| 6,303,121 B1 | 10/2001 | Kwon | |
| 7,070,995 B2 | 7/2006 | Jensen | |
| 7,435,596 B2 | 10/2008 | Campana et al. | |
| 7,446,190 B2 | 11/2008 | Sadelain et al. | |
| 8,026,097 B2 | 9/2011 | Campana et al. | |
| 2003/0147869 A1 | 8/2003 | Riley et al. | |
| 2003/0215427 A1* | 11/2003 | Jensen ................... | 424/93.21 |
| 2004/0038886 A1 | 2/2004 | Finney et al. | |
| 2004/0043401 A1* | 3/2004 | Sadelain et al. .......... | 435/6 |
| 2004/0126363 A1* | 7/2004 | Jensen et al. ............ | 424/93.21 |
| 2005/0113564 A1 | 5/2005 | Campana et al. | |
| 2012/0015434 A1 | 1/2012 | Campana et al. | |

OTHER PUBLICATIONS

Imai et al. (Blood, 102 (11): p. 66a-67a; Nov. 16, 2003).*
Imai et al. (Journal of Biological Regulators and Homeostatic Agents, 18 (1): p. 62-71; Jan. 2004; abstract only).*
Koehler et al. (Advances in Hematology, vol. 2012, Article ID 595060, 13 pages; doi:10.1155/2012/595060.*

Alderson MR, et. al., "Molecular and biological characterization of human 4-1BB and its ligand. Eur J Immunol", Sep. 1994; 24 (9) :2219-27.
Brentjens RJ, et. al., "Eradication of systemic B-cell tumors by genetically targeted human T lymphocytes co-stimulated by CD80 and interleukin-15", Nat Med. Mar. 2003; 9 (3) :279-86.
Bukczynski J, et. al., "Costimulation of human CD28- T cells by 4-1BB ligand", Eur J Immunol. Feb. 2003; 33 (2) :446-54.
Burkett PR, et. al., "Coordinate expression and trans presentation of interleukin (IL)-15Ralpha and IL-15 supports natural killer cell and memory CD8+ T cell homeostasis", J Exp Med. Oct. 4, 2004; 200 (7):825-34.
Campana D, et. al., "Immunophenotyping of leukemia. J Immunol Methods", Sep. 21, 2000; 243 (1-2):59-75.
Carson WE, et. al., "A potential role for interleukin-15 in the regulation of human natural killer cell survival", J Clin Invest. Mar. 1, 1997; 99 (5) :937-43.
Cheung NK, et. al., "Anti-idiotypic antibody facilitates scFv chimeric immune receptor gene transduction and clonal expansion of human lymphocytes for tumor therapy. Hybrid Hybridomics", Aug. 2003; 22 (4) :209-18.
Cooper LJ, et. al., "T-cell clones can be rendered specific for CD19: toward the selective augmentation of the graft-versus-B-lineage leukemia effect", Blood. Feb. 15, 2003; 101 (4) :1637-44.
Cooper MA, et. al., "In vivo evidence for a dependence on interleukin 15 for survival of natural killer cells", Blood. Nov. 15, 2002; 100 (10) :3633-8.
DeBenedette MA, et. al., "Costimulation of CD28- T lymphocytes by 4-1BB ligand. J Immunol", Jan. 15, 1997; 158 (2) :551-9.
Eshhar Z, et. al., "Functional expression of chimeric receptor genes in human T cells", J Immunol Methods. Feb. 1, 2001; 248 (1-2) :67-76.
Farag SS, et. al., "Natural killer cell receptors: new biology and insights into the graft-versus-leukemia effect", Blood. Sep. 15, 2002; 100 (6) :1935-47.
Fehniger TA, et. al.; "Ontogeny and expansion of human natural killer cells: clinical implications", Int Rev Immunol. Jun. 2001; 20 (3-4) :503-34.
Finney HM, et. al., "Activation of resting human primary T cells with chimeric receptors: costimulation from CD28, inducible costimulator, CD134, and CD137 in series with signals from the TCR zeta chain", J Immunol. Jan. 1, 2004; 172 (1) :104-13.
Geiger TL, et. al., "Integrated src kinase and costimulatory activity enhances signal transduction through single-chain chimeric receptors in T lymphocytes", Blood. Oct. 15, 2001; 98 (8) :2364-71.
Goodwin RG, et. al., "Molecular cloning of a ligand for the inducible T cell gene 4-1BB: a member of an emerging family of cytokines with homology to tumor necrosis factor", Eur J Immunol. Oct. 1993; 23 (10) :2631-41.
Greenwald RJ, et. al., "The B7 family revisited", Annu Rev Immunol. 2005; 23:515-48.

(Continued)

*Primary Examiner* — Ilia Ouspenski
(74) *Attorney, Agent, or Firm* — Jones Day

(57) ABSTRACT

The present invention relates to a chimeric receptor capable of signaling both a primary and a co-stimulatory pathway, thus allowing activation of the co-stimulatory pathway without binding to the natural ligand. The cytoplasmic domain of the receptor contains a portion of the 4-1BB signaling domain. Embodiments of the invention relate to polynucleotides that encode the receptor, vectors and host cells encoding a chimeric receptor, particularly including T cells and natural killer (NK) cells and methods of use.

22 Claims, 2 Drawing Sheets

OTHER PUBLICATIONS

Figure 1:
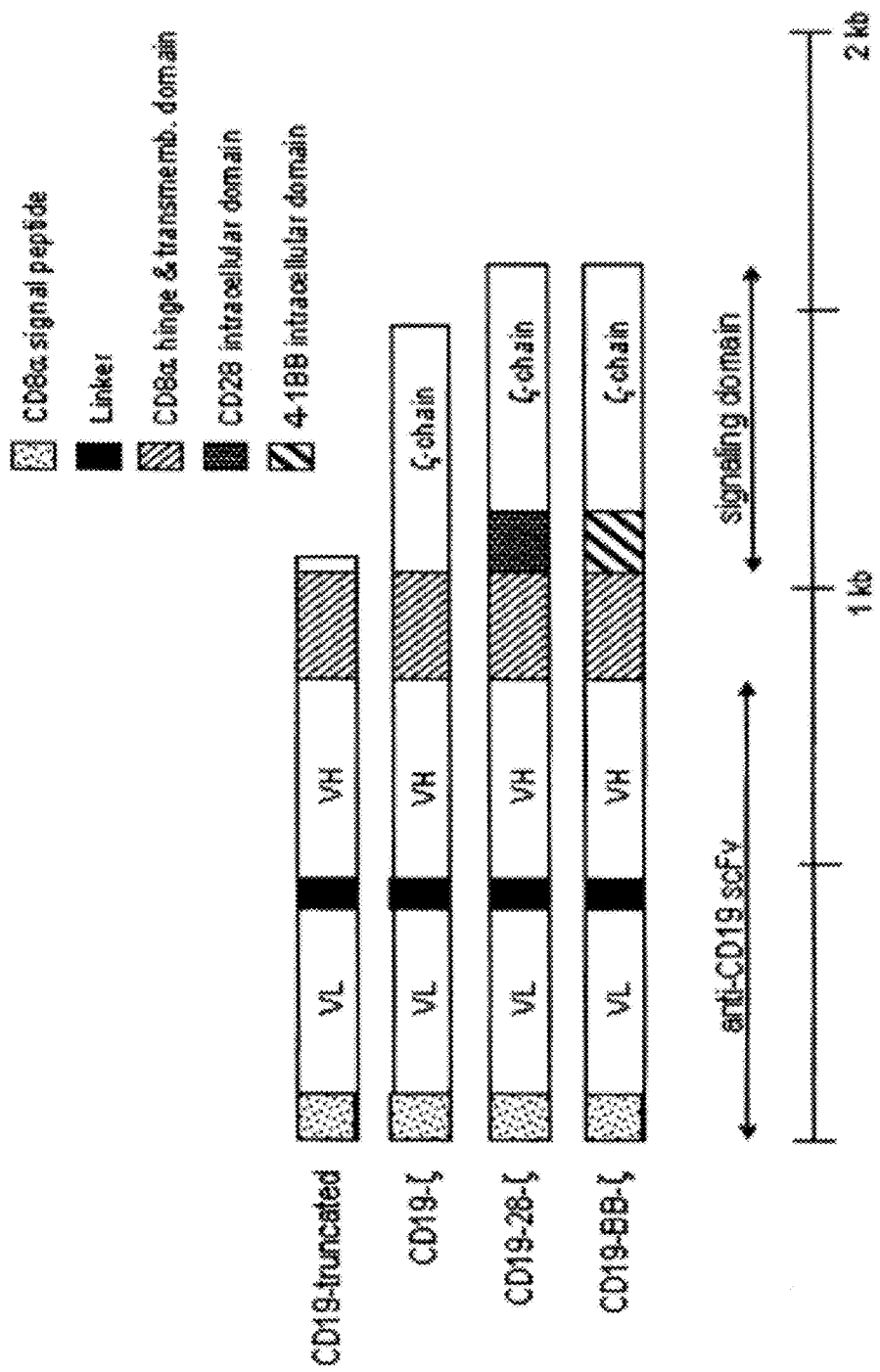

Harada H, et. al.; "A Wilms tumor cell line, HFWT, can greatly stimulate proliferation of CD56+ human natural killer cells and their novel precursors in blood mononuclear cells", Exp Hematol. Jul. 2004; 32 (7) :614-21.

Harada H, et. al., "Selective expansion of human natural killer cells from peripheral blood mononuclear cells by the cell line, HFWT", Jpn J Cancer Res. Mar. 2002; 93 (3) :313-9.

Haynes NM, et. al., "Single-chain antigen recognition receptors that costimulate potent rejection of established experimental tumors", Blood. Nov. 1, 2002; 100 (9) :3155-63.

Haynes NM, et. al., "Rejection of syngeneic colon carcinoma by CTLs expressing single-chain antibody receptors codelivering CD28 costimulation", J Immunol. Nov. 15; 169 (10) :5780-6.

Hombach , et. al., "Tumor-specific T cell activation by recombinant immunoreceptors: CD3 zeta signaling and CD28 costimulation are simultaneously required for efficient IL-2 secretion and can be integrated into one combined CD28/CD3 zeta signaling receptor molecule", J Immunol. Dec. 1, 2001; 167 (11) :6123-31.

Hurtado JC, et. al., "Signals through 4-1BB are costimulatory to previously activated splenic T cells and inhibit activation-induced cell death", J Immunol. Mar. 15, 1997; 158 (6) :2600-9.

Imai C, et. al., "A novel method for propagating primary natural killer (NK) cells allows highly efficient expression of anti-CD19 chimeric receptors and generation of powerful cytotoxicity against NK-resistant acute lymphoblastic leukemia cells", Abstract No. 306, Blood 104 (Nov. 2004).

Ishiwata I, et. al., "Carcinoembryonic proteins produced by Wilms' tumor cells in vitro and in vivo", Exp Pathol. 1991; 41 (1) :1-9.

Kim YJ, et. al., "Human 4-1BB regulates CD28 co-stimulation to promote Th1 cell responses. Eur J Immunol", Mar. 1998; 28 (3) :881-90.

Kim YJ, et. al., "Novel T cell antigen 4-1BB associates with the protein tyrosine kinase p56Ick1", J Immunol. Aug. 1, 1993; 151 (3) :1255-62.

Klein E, et. al., "Properties of the K562 cell line, derived from a patient with chronic myeloid leukemia", Int J Cancer. Oct. 15, 1976; 18 (4) :421-31.

Klingemann HG, et. al., "Ex vivo expansion of natural killer cells for clinical applications", Cytotherapy. 2004; 6 (1) :15-22.

Kwon BS, et. al., "cDNA sequences of two inducible T-cell genes", Proc Natl Aced Sci U S A. Mar. 1989; 86 (6) :1963-7.

Li Q, et. al., "Polarization effects of 4-1BB during CD28 costimulation in generating tumor-reactive T cells for cancer immunotherapy", Cancer Res. May 15, 2003; 63 (10) :2546-52.

Lozzio Lozzio CB, et. al., "Human chronic myelogenous leukemia cell-line with positive Philadelphia chromosome", Blood. Mar. 1975; 45 (3) :321-34.

Maher J, et. al., "Human T-lymphocyte cytotoxicity and proliferation directed by a single chimeric TCRzeta /CD28 receptor", Nat Biotechnol. Jan. 2002; 20 (1) :70-5.

Martinet O, , et. al., "T cell activation with systemic agonistic antibody versus local 4-1BB ligand gene delivery combined with interleukin-12 eradicate liver metastases of breast cancer", Gene Ther. Jun. 2002; 9 (12) :786-92.

Maus MV, et. al., "Ex vivo expansion of polyclonal and antigen-specific cytotoxic T lymphocytes by artificial APCs expressing ligands for the T-cell receptor, CD28 and 4-1BB", Nat Biotechnol. Feb. 2002; 20 (2) :143-8.

May KF Jr, et. al., "Anti-4-1BB monoclonal antibody enhances rejection of large tumor burden by promoting survival but not clonal expansion of tumor-specific CD8+ T cells", Cancer Res. Jun. 15, 2002; 62 (12) :3459-65.

Melero I, et. al., "Amplification of tumor immunity by gene transfer of the co-stimulatory 4-1BB ligand: synergy with the CD28 co-stimulatory pathway", Eur J Immunol. Mar. 1998; 28 (3) :1116-21.

Melero I, et. al., "Monoclonal antibodies against the 4-1BB T-cell activation molecule eradicate established tumors", Nat Med. Jun. 1997; 3 (6) :682-5.

Melero I, et. al., "NK1.1 cells express 4-1BB (CDw137) costimulatory molecule and are required for tumor immunity elicited by anti-4-1BB monoclonal antibodies", Cell Immunol. Dec. 15, 1998; 190 (2) :167-72.

Moretta L, et. al., "Unravelling natural killer cell function: triggering and inhibitory human NK receptors", EMBO J. Jan. 28, 2004; 23 (2) :255-9.

Nicholson IC, et. al., "Construction and characterisation of a functional CD19 specific single chain Fv fragment for immunotherapy of B lineage leukaemia and lymphoma", Mol Immunol. Nov.-Dec. 1997; 34 (16-17) :1157-65.

Oelke M, et. al., "Ex vivo induction and expansion of antigen-specific cytotoxic T cells by HLA-Ig-coated artificial antigen-presenting cells", Nat Med. May 2003; 9 (5) :619-24.

Pollok KE, et. al., "Inducible T cell antigen 4-1BB Analysis of expression and function", J Immunol. Feb. 1, 1993; 150 (3) :771-81.

Riley JL, et. al., "The CD28 family: a T-cell rheostat for therapeutic control of T-cell activation", Blood. Jan. 1, 2005; 105 (1) :13-21.

Robertson MJ, et. al.; "Costimulation of human natural killer cell proliferation: role of accessory cytokines and cell contact-dependent signals", Nat Immun. 1996-1997; 15 (5) :213-26.

Shuford WW, et. al., "4-1BB costimulatory signals preferentially induce CD8+ T cell proliferation and lead to the amplification in vivo of cytotoxic T cell responses", J Exp Med. Jul. 7, 1997; 186 (1) :47-55.

Takahashi C, et. al., "Cutting edge: 4-1BB is a bona fide CD8 T cell survival signal", J Immunol. May 1, 1999; 162 (9) :5037-40.

Vinay DS, et. al., "Role of 4-1BB in immune responses", Semin Immunol. Dec. 1998; 10 (6) :481-9.

Zeis M, et. al., "Allogeneic MHC-mismatched activated natural killer cells administered after bone marrow transplantation provide a strong graft-versus-leukaemia effect in mice", Br J Haematol. Mar. 1997; 96 (4) :757-61.

ATCC No. CCL-243, 1975.

Office Action of U.S. Appl. No. 10/981,352, dated Jan. 4, 2008.

Office Action of U.S. Appl. No. 10/981,352, dated Jun. 7, 2007.

Response to Election of Species Requirement of Office Action of U.S. Appl. No. 10/981,352, dated Mar. 27, 2007.

Office Action of U.S. Appl. No. 10/981,352, dated Mar. 14, 2007.

Response to Restriction Requirement of Office Action of U.S. Appl. No. 10/981,352, dated Dec. 27, 2006.

Office Action of U.S. Appl. No. 10/981,352, dated Nov. 29, 2006.

* cited by examiner

US 8,399,645 B2

CHIMERIC RECEPTORS WITH 4-1BB STIMULATORY SIGNALING DOMAIN

2. CROSS-REFERENCE TO RELATED APPLICATIONS

This application is a continuation of U.S. application Ser. No. 13/244,981, filed Sep. 26, 2011 now abandoned, which is a continuation of U.S. patent application Ser. No. 12/206,204, filed on Sep. 8, 2008 (granted as U.S. Pat. No. 8,026,097), which is a continuation of U.S. patent application Ser. No. 11/074,525, filed on Mar. 8, 2005 (granted as U.S. Pat. No. 7,435,596), which is a continuation-in-part of U.S. patent application Ser. No. 10/981,352 filed Nov. 4, 2004 (abandoned), which claims the benefit of U.S. Provisional Patent Application Ser. No. 60/517,507 filed on Nov. 5, 2003, each of which is incorporated herein by reference in its entirety.

The instant application contains a Sequence Listing which has been submitted in ASCII format via EFS-Web and is hereby incorporated by reference in its entirety. The Sequence Listing is being concurrently submitted via EFS-Web as an ASCII text file named 13213-005-999_Sequence_Listing.txt, created Jul. 12, 2012, and being 16,298 bytes in size.

1. GOVERNMENT INTEREST

This invention was made in part with U.S. Government support under National Institutes of Health grant No. CA 58297. The U.S. Government may have certain rights in this invention.

3. FIELD OF THE INVENTION

This invention relates to chimeric cell membrane receptors, particularly chimeric T-cell receptors. This invention further relates to activation and expansion of cells for therapeutic uses, in particular for activation and expansion of NK cells for chimeric receptor-based cell therapy.

4. BACKGROUND

Regulation of cell activities is frequently achieved by the binding of a ligand to a surface membrane receptor comprising an extracellular and a cytoplasmic domain. The formation of the complex between the ligand and the extracellular portion of the receptor results in a conformational change in the cytoplasmic portion of the receptor which results in a signal transduced within the cell. In some instances, the change in the cytoplasmic portion results in binding to other proteins, where other proteins are activated and may carry out various functions. In some situations, the cytoplasmic portion is autophosphorylated or phosphorylated, resulting in a change in its activity. These events are frequently coupled with secondary messengers, such as calcium, cyclic adenosine monophosphate, inositol phosphate, diacylglycerol, and the like. The binding of the ligand to the surface membrane receptor results in a particular signal being transduced.

For T-cells, engagement of the T-cell receptor (TCR) alone is not sufficient to induce persistent activation of resting naive or memory T cells. Full, productive T cell activation requires a second co-stimulatory signal from a competent antigen-presenting cell (APC). Co-stimulation is achieved naturally by the interaction of the co-stimulatory cell surface receptor on the T cell with the appropriate counter-receptor on the surface of the APC. An APC is normally a cell of host origin which displays a moiety which will cause the stimulation of an immune response. APCs include monocyte/macrophages, dendritic cells, B cells, and any number of virally-infected or tumor cells which express a protein on their surface recognized by T cells. To be immunogenic APCs must also express on their surface a co-stimulatory molecule. Such APCs are capable of stimulating T cell proliferation, inducing cytokine production, and acting as targets for cytolytic T cells upon direct interaction with the T cell. See Linsley and Ledbetter, Ann. Rev. Immunol. 4:191-212 (1993); Johnson and Jenkins, Life Sciences 55:1767-1780 (1994); June et al., Immunol. Today 15:321-331 (1994); and Mondino and Jenkins, J. Leuk. Biol. 55:805-815 (1994).

Engagement of the co-stimulatory molecule together with the TCR is necessary for optimal levels of IL-2 production, proliferation and clonal expansion, and generation of effector functions such as the production of immunoregulatory cytokines, induction of antibody responses from B cells, and induction of cytolytic activity. More importantly, engagement of the TCR in the absence of the co-stimulatory signal results in a state of non-responsiveness, called anergy. Anergic cells fail to become activated upon subsequent stimulation through the TCR, even in the presence of co-stimulation, and in some cases may be induced to die by a programmed self-destruct mechanism.

In certain situations, for example where APCs lack the counter-receptor molecules necessary for co-stimulation, it would be beneficial to have the co-stimulatory signal induced by virtue of employing a ligand other than the natural ligand for the co-stimulatory receptor. This might be, for example, the same ligand as that recognized by the TCR (i.e., the same moiety, such that if one signal is received, both signals will be received), or another cell surface molecule known to be present on the target cells (APCs).

Several receptors that have been reported to provide co-stimulation for T-cell activation, including CD28, OX40, CD27, CD2, CD5, ICAM-1, LFA-1 (CD11a/CD18), and 4-1BB. The signaling pathways utilized by these co-stimulatory molecules share the common property of acting in synergy with the primary T cell receptor activation signal.

Previously the signaling domain of CD28 has been combined with the T-cell receptor to form a co-stimulatory chimeric receptor. See U.S. Pat. No. 5,686,281; Geiger, T. L. et al., *Blood* 98: 2364-2371 (2001); Hombach, A. et al., *J Immunol* 167: 6123-6131 (2001); Maher, J. et al. *Nat Biotechnol* 20: 70-75 (2002); Haynes, N. M. et al., *J Immunol* 169: 5780-5786 (2002); Haynes, N. M. et al., *Blood* 100: 3155-3163 (2002). These co-stimulatory receptors provide a signal that is synergistic with the primary effector activation signal, i.e. the TCR signal or the chimeric effector function receptor signal, and can complete the requirements for activation under conditions where stimulation of the TCR or chimeric effector function receptor is suboptimal and might otherwise be detrimental to the function of the cell. These receptors can support immune responses, particularly of T cells, by permitting the use of ligands other than the natural ligand to provide the required co-stimulatory signal.

Chimeric receptors that contain a CD19 specific single chain immunoglobulin extracellular domain have been shown to lyse CD19+ target cells and eradicate CD19+ B cell lymphomas engrafted in mice [Cooper L J, et al., Blood 101:1637-1644 (2003) and Brentjens R J, et al., Nature Medicine 9:279-286 (2003)]. Cooper et al. reported that T-cell clones transduced with chimeric receptors comprising anti-CD19 scFv and CD3ζ produced approximately 80% specific lysis of B-cell leukemia and lymphoma cell lines at a 1:1 effector to target ratio in a 4-hour Cr release assay; at this ratio, percent specific lysis of one primary B-lineage ALL sample tested was approximately 30%. Brentjens et al. reported that T-cells bearing anti-CD19 scFv and CD3ζ chimeric receptors could be greatly expanded in the presence of exogenous IL-15 and artificial antigen-presenting cells transduced with CD19 and CD80. The authors showed that these T cells significantly improved the survival of immunodeficient mice engrafted with the Raji B-cell lymphoma cell line. Their results also confirmed the importance of co-stimulation in maximizing T-cell-mediated anti-leukemic activity. Only cells expressing the B7 ligands of CD28 elicited effective T-cell responses. This could be a major obstacle in the case of B-lineage ALL because leukemic lymphoblasts typically do not express B7 molecules.

In addition to T cell immune responses, natural killer (NK) cell responses appear to be clinically relevant. While T cells recognize tumor associated peptide antigen expressed on surface HLA class I or class II molecules, antigen nonspecific immune responses are mediated by NK cells that are activated by the failure to recognize cognate "self" HLA class I molecules. The graft-versus-tumor effect of transplants using HLA matched donors is mediated by antigen specific T cells, while transplantation using HLA mismatched donors can also lead to donor NK cells with potent antitumor activity. HLA mismatched haplo-identical transplants can exert a powerful anti-leukemia effect based on expansion of antigen nonspecific donor NK cells.

Immunotherapy with NK cells has been limited by the inability to obtain sufficient numbers of pure NK cells suitable for manipulation and expansion. The established methods for cell expansion favor T cell expansion and even after T cells are depleted, residual T cells typically become prominent after stimulation. Thus there is a need for better methods to expand NK cells from a population without expanding T cells.

5. SUMMARY OF THE INVENTION

The present invention provides a chimeric receptor containing a co-stimulatory signal by incorporation of the signaling domain of the 4-1BB receptor. The chimeric receptor comprises an extracellular ligand binding domain, a transmembrane domain and a cytoplasmic domain wherein the cytoplasmic domain comprises the signaling domain of 4-1BB. In one embodiment of the invention the signaling domain of 4-1BB used in the chimeric receptor is of human origin. In a preferred embodiment, human 4-1BB consists of SEQ ID NO:2. In another embodiment the signaling domain comprises amino acids 214-255 of SEQ ID NO:2.

In another embodiment of the invention the cytoplasmic domain of the chimeric receptor comprises the signaling domain of CD3ζ in addition to the signaling domain of 4-1BB. In another embodiment the extracellular domain comprises a single chain variable domain of an anti-CD19 monoclonal antibody. In another embodiment the transmembrane domain comprises the hinge and transmembrane domains of CD8α. In a most preferred embodiment of the invention the extracellular domain comprises a single chain variable domain of an anti-CD19 monoclonal antibody, the transmembrane domain comprises the hinge and transmembrane domain of CD8α, and the cytoplasmic domain comprises the signaling domain of CD3ζ and the signaling domain of 4-1BB.

Other aspects of the invention include polynucleotide sequences, vectors and host cells encoding a chimeric receptor that comprises the signaling domain of 4-1BB. Yet other aspects include methods of enhancing T lymphocyte or natural killer (NK) cell activity in an individual and treating an individual suffering from cancer by introducing into the individual a T lymphocyte or NK cell comprising a chimeric receptor that comprises the signaling domain of 4-1BB. These aspects particularly include the treatment of lung cancer, melanoma, breast cancer, prostate cancer, colon cancer, renal cell carcinoma, ovarian cancer, neuroblastoma, rhabdomyosarcoma, leukemia and lymphoma. Preferred cancer targets for use with the present invention are cancers of B cell origin, particularly including acute lymphoblastic leukemia, B-cell chronic lymphocytic leukemia and B-cell non-Hodgkin's lymphoma.

A different but related aspect of the present invention provides a method for obtaining an enriched NK cell population suitable for transduction with a chimeric receptor that comprises the signaling domain of 4-1BB. This method comprises the expansion of NK cells within a mixed population of NK cells and T cells by co-culturing the mixed population of cells with a cell line that activates NK cells and not T lymphocytes. This NK activating cell line is composed of cells that activate NK cells, but not T lymphocytes, and which express membrane bound interleukin-15 and a co-stimulatory factor ligand. In a particular embodiment the NK activating cell line is the K562 myeloid leukemia cell line or the Wilms tumor cell line HFWT. In another embodiment of the invention the co-stimulatory factor ligand is CD137L.

Another aspect of the present invention is based on the concept that expression of chimeric receptors on NK cells could overcome HLA-mediated inhibitory signals, thus endowing the cells with cytotoxicity against otherwise NK-resistant cells. The invention provides a method that allows specific and vigorous preferential expansion of NK cells lacking T-cell receptors (CD56$^+$ CD3$^-$ cells) and their highly efficient transduction with chimeric receptors.

6. DESCRIPTION OF THE SEQUENCE LISTING

SEQ ID No. 1 is the nucleotide sequence for human 4-1BB mRNA. The coding sequence for the human 4-1BB protein begins at position 129 and ends at position 893.

SEQ ID No. 2 is the amino acid sequence of human 4-1BB. The signaling domain begins at position 214 and ends at position 255.

SEQ. ID. No. 3 is the nucleotide sequence for murine 4-1BB mRNA. The coding sequence for the murine 4-1BB protein begins at position 146 and ends at position 916.

SEQ ID. No. 4 is the amino acid sequence of murine 4-1BB. The signaling domain begins at position 209 and ends at position 256.

7. DESCRIPTION OF THE FIGURES

FIG. 1 is a schematic representation of the CD19-truncated, CD19-ζ, CD19-28-ζ and CD19-BB-ζ receptor constructs.

Figure 2:
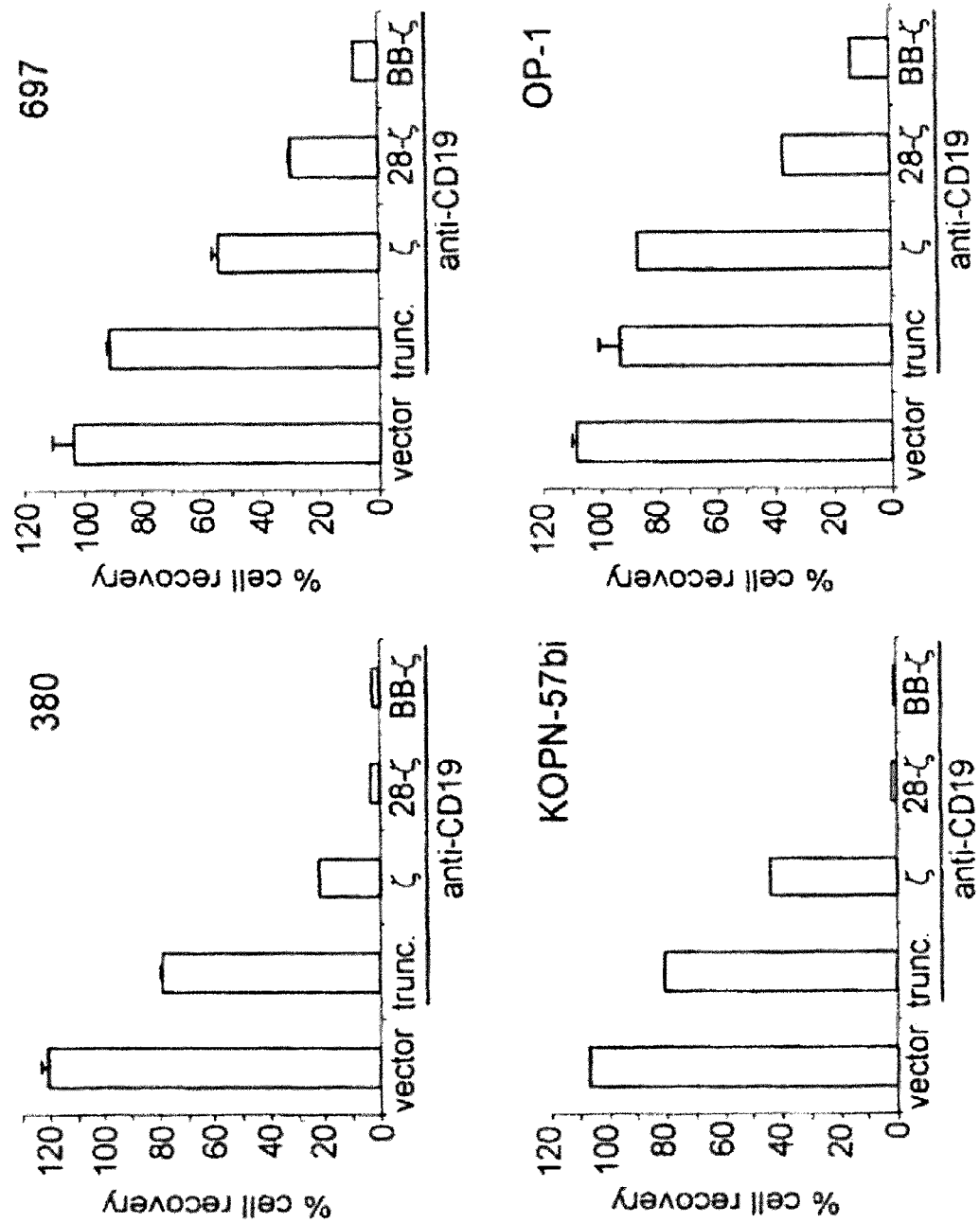

FIG. 2 shows the percent of CD19-positive leukemia cell recovery in four different cell lines (380, 697, KOPN-57bi and OP-1) after 24 hours of culture with NK cells with or without a chimeric receptor at a 1:1 ratio relative to cultures with no NK cells. The bars represent each of the 4 cell lines that are co-cultured with NK cells containing either "vector" which is MSCV-IRES GFP only; "trunc." which is vector containing truncated anti-CD19; "ζ" which is vector containing anti-CD19-CD3ζ; "28 ζ" which is vector containing anti-CD19-CD28α-CD3ζ; or "BB-ζ" which is vector containing anti-CD19-4-1BB intracellular domain-CD3ζ. This figure shows that chimeric receptors confer anti-ALL activity to NK cells which is improved by the addition of the co-stimulatory molecules CD28 or 4-1BB.

8. DETAILED DESCRIPTION OF THE INVENTION

Definitions 4-1BB: The term "4-1BB" refers to a membrane receptor protein also termed CD137, which is a member of the tumor necrosis factor receptor (TNFR) superfamily expressed on the surface of activated T-cells as a type of accessory molecule [Kwon et al., Proc. Natl. Acad. Sci. USA 86:1963 (1989); Pollok et al., J. Immunol. 151:771 (1993)]. 4-1BB has a molecular weight of 55 kDa, and is found as a homodimer. It has been suggested that 4-1BB mediates a signal transduction pathway from outside of the cell to inside [Kim et al., J. Immunol. 151:1255 (1993)].

A human 4-1BB gene (SEQ ID NO:1) was isolated from a cDNA library made from activated human peripheral T-cell mRNA [Goodwin et al., Eur. J. Immunol. 23:2631 (1993);]. The amino acid sequence of human 4-1BB (SEQ ID NO: 2) shows 60% homology to mouse 4-1BB (SEQ ID NO:4) [Kwon et al., Proc. Natl. Acad. Sci. USA 86:1963 (1989); Gen Bank No: NM_011612] which indicates that the sequences are highly conserved. As mentioned supra, 4-1BB belongs to the TNFR superfamily, along with CD40, CD27, TNFR-I, TNFR-II, Fas, and CD30 [Alderson et al., Eur. J. Immunol. 24:2219 (1994)]. When a monoclonal antibody is bound to 4-1BB expressed on the surface of mouse T-cells, anti-CD3 T-cell activation is increased many fold [Pollok et al., J. Immunol. 150:771 (1993)].

4-1BB binds to a high-affinity ligand (4-1BB, also termed CD137L) expressed on several antigen-presenting cells such as macrophages and activated B cells [Pollok et al., J. Immunol. 150:771 (1993) Schwarz et al., Blood 85:1043 (1995)). The interaction of 4-1BB and its ligand provides a co-stimulatory signal leading to T cell activation and growth [Goodwin et al., Eur. J. Immunol. 23:2631 (1993); Alderson et al., Eur. J. Immunol. 24:2219 (1994); Hurtado et al., J. Immunol. 155:3360 (1995); Pollock et al., Eur. J. Immunol. 25:488 (1995); DeBenedette et al., J. Exp. Med. 181:985 (1995)]. These observations suggest an important role for 4-1BB in the regulation of T cell-mediated immune responses [Ignacio et al., Nature Med. 3:682 (1997)].

4-1BB ligand (CD137L) is claimed and described in U.S. Pat. No. 5,674,704.

The term IL-15 (interleukin 15) refers to a cytokine that stimulates NK cells [Fehniger T A, Caligiuri M A. Blood 97(1):14-32 (2001)]. It has become apparent that IL-15 presented through cell-to-cell contact has a higher NK stimulating activity than soluble IL-15 [Dubois S, et al., Immunity 17(5):537-547 (2002); Kobayashi H, et al., Blood (2004) PMID: 15367431; Koka R, et al., J Immunol 173(6):3594-3598 (2004); Burkett P R, et al., J Exp Med 200(7):825-834 (2004)]. To express membrane-bound IL-15 a construct consisting of human IL-15 mature peptide (NM 172174) was fused to the signal peptide and transmembrane domain of human CD8α.

To specifically or preferentially expand NK cells means to culture a mixed population of cells that contains a small number of NK cells so that the NK cells proliferate to numbers greater than other cell types in the population.

To activate T cells and NK cells means to induce a change in their biologic state by which the cells express activation markers, produce cytokines, proliferate and/or become cytotoxic to target cells. All these changes can be produced by primary stimulatory signals. Co-stimulatory signals amplify the magnitude of the primary signals and suppress cell death following initial stimulation resulting in a more durable activation state and thus a higher cytotoxic capacity.

The terms T-cell and T lymphocyte are interchangeable and used synonymously herein.

The term "chimeric receptor" as used herein is defined as a cell-surface receptor comprising an extracellular ligand binding domain, a transmembrane domain and a cytoplasmic co-stimulatory signaling domain in a combination that is not naturally found together on a single protein. This particularly includes receptors wherein the extracellular domain and the cytoplasmic domain are not naturally found together on a single receptor protein. The chimeric receptors of the present invention are intended primarily for use with T cells and natural killer (NK) cells.

The term "host cell" means any cell of any organism that is selected, modified, transformed, grown, used or manipulated in any way, for the production of a substance by the cell, for example the expression by the cell of a gene, a DNA or RNA sequence, a protein or an enzyme. Host cells of the present invention include T cells and NK cells that contain the DNA or RNA sequences encoding the chimeric receptor and express the chimeric receptor on the cell surface. Host cells may be used for enhancing T lymphocyte activity, NK cell activity, treatment of cancer, and treatment of autoimmune diseases.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. An expression product can be characterized as intracellular, extracellular or transmembrane. The term "intracellular" means something that is inside a cell. The term "extracellular" means something that is outside a cell. The term transmembrane means something that has an extracellular domain outside the cell, a portion embedded in the cell membrane and an intracellular domain inside the cell.

The term "transfection" means the introduction of a foreign nucleic acid into a cell using recombinant DNA technology. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The term "transduction" means the introduction of a foreign nucleic acid into a cell using a viral vector.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Vectors include plasmids, phages, viruses, etc.

A solid support means any surface capable of having an agent attached thereto and includes, without limitation, metals, glass, plastics, polymers, particles, microparticles, copolymers, colloids, lipids, lipid bilayers, cell surfaces and the like. Essentially any surface that is capable of retaining an agent bound or attached thereto. A prototypical example of a solid support used herein, is a particle such as a bead.

The term "substantially free of" means a population of cells, e.g. NK cells, that is at least 50% free of non-NK cells, or in certain embodiments at least 60, 70, 80, 85, or 90% free of non-NK cells.

A "co-stimulatory signal" refers to a signal, which in combination with a primary signal, such as TCR/CD3 ligation, leads to NK cell proliferation and/or upregulation or downregulation of key molecules.

Description of the Invention

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes [-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Haines & S. J. Higgins eds. (1985)]; "Transcription And Translation" [B. D. Haines & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984); CURRENT PROTOCOLS IN IMMUNOLOGY Q. E. Coligan, A. M. Kruisbeek, D. H. Margulies, E. M. Shevach and W. Strober, eds., 1991); ANNUAL REVIEW OF IMMUNOLOGY; as well as monographs in journals such as ADVANCES IN IMMUNOLOGY. All patents, patent applications, and publications mentioned herein are hereby incorporated herein by reference.

Primary T cells expressing chimeric receptors specific for tumor or viral antigens have considerable therapeutic potential as immunotherapy reagents. Unfortunately, their clinical value is limited by their rapid loss of function and failure to expand in vivo, presumably due to the lack of co-stimulator molecules on tumor cells and the inherent limitations of signaling exclusively through the chimeric receptor.

The chimeric receptors of the present invention overcome this limitation wherein they have the capacity to provide both the primary effector activity and the co-stimulatory activity upon binding of the receptor to a single ligand. For instance, binding of the anti-CD19-BB-ζ receptor to the CD19 ligand provides not only the primary effector function, but also a proliferative and cytolytic effect.

T cells transduced with anti-CD19 chimeric receptors of the present invention which contain co-stimulatory molecules have remarkable anti-ALL capacity. However, the use of allogenic receptor-modified T cells after hematopoietic cell transplantation might carry the risk of severe graft-versus-host disease (GvHD). In this setting, the use of CD3-negative NK cells is attractive because they are not expected to cause GvHD.

Studies suggest an anti-tumor effect of NK cells and Zeis et al., Br J Haematol 96: 757-61 (1997) have shown in mice that NK cells contribute to a graft-versus-leukemia effect, without inducing GvHD.

Expanding NK cells which can then be transfected with chimeric receptors according to this method represents another aspect of the present invention.

The chimeric receptors of the present invention comprise an extracellular domain, a transmembrane domain and a cytoplasmic domain. The extracellular domain and transmembrane domain can be derived from any desired source for such domains.

As described in U.S. Pat. Nos. 5,359,046, 5,686,281 and 6,103,521, the extracellular domain may be obtained from any of the wide variety of extracellular domains or secreted proteins associated with ligand binding and/or signal transduction. The extracellular domain may be part of a protein which is monomeric, homodimeric, heterodimeric, or associated with a larger number of proteins in a non-covalent complex. In particular, the extracellular domain may consist of an Ig heavy chain which may in turn be covalently associated with Ig light chain by virtue of the presence of CH1 and hinge regions, or may become covalently associated with other Ig heavy/light chain complexes by virtue of the presence of hinge, CH2 and CH3 domains. In the latter case, the heavy/light chain complex that becomes joined to the chimeric construct may constitute an antibody with a specificity distinct from the antibody specificity of the chimeric construct. Depending on the function of the antibody, the desired structure and the signal transduction, the entire chain may be used or a truncated chain may be used, where all or a part of the CH1, CH2, or CH3 domains may be removed or all or part of the hinge region may be removed.

Wherein an antitumor chimeric receptor is utilized, the tumor may be of any kind as long as it has a cell surface antigen which may be recognized by the chimeric receptor. In a specific embodiment, the chimeric receptor may be for any cancer for which a specific monoclonal antibody exists or is capable of being generated. In particular, cancers such as neuroblastoma, small cell lung cancer, melanoma, ovarian cancer, renal cell carcinoma, colon cancer, Hodgkin's lymphoma, and childhood acute lymphoblastic leukemia have antigens specific for the chimeric receptors.

The transmembrane domain may be contributed by the protein contributing the multispecific extracellular inducer clustering domain, the protein contributing the effector function signaling domain, the protein contributing the proliferation signaling portion, or by a totally different protein. For the most part it will be convenient to have the transmembrane domain naturally associated with one of the domains. In some cases it will be desirable to employ the transmembrane domain of the .zeta., .eta. or Fc.epsilon.R1.gamma. chains which contain a cysteine residue capable of disulfide bonding, so that the resulting chimeric protein will be able to form disulfide linked dimers with itself, or with unmodified versions of the .zeta., .eta. or Fc.epsilon.R1.gamma. chains or related proteins. In some instances, the transmembrane domain will be selected or modified by amino acid substitution to avoid binding of such domains to the transmembrane domains of the same or different surface membrane proteins to minimize interactions with other members of the receptor complex. In other cases it will be desirable to employ the transmembrane domain of .zeta., .eta., Fc.epsilon.R1-.gamma. and -.beta., MB1 (Ig.alpha.), B29 or CD3-.gamma., .zeta., or .epsilon., in order to retain physical association with other members of the receptor complex.

The cytoplasmic domain of the chimeric receptors of the invention will comprise the 4-1BB signaling domain by itself or combined with any other desired cytoplasmic domain(s) useful in the context of this chimeric receptor type. In a most preferred embodiment of the invention the extracellular domain comprises a single chain variable domain of an anti-CD19 monoclonal antibody, the transmembrane domain comprises the hinge and transmembrane domain of CD8α, and the cytoplasmic domain comprises the signaling domain of CD3ζ and the signaling domain of 4-1BB. The extracellular domain of the preferred embodiment contains the anti-CD19 monoclonal antibody which is described in Nicholson IC, et al., Mol Immunol 34:1157-1165 (1997) plus the 21 amino acid signal peptide of CD8α (translated from 63 nucleotides at positions 26-88 of GenBank Accession No. NM_001768). The CD8α hinge and transmembrane domain consists of 69 amino acids translated from the 207 nucleotides at positions 815-1021 of GenBank Accession No. NM_001768. The CD3ζ signaling domain of the preferred embodiment contains 112 amino acids translated from 339 nucleotides at positions 1022-1360 of GenBank Accession No. NM_000734.

Antigen-specific cells can be expanded in vitro for use in adoptive cellular immunotherapy in which infusions of such cells have been shown to have anti-tumor reactivity in a tumor-bearing host. The compositions and methods of this invention can be used to generate a population of T lymphocyte or NK cells that deliver both primary and co-stimulatory signals for use in immunotherapy in the treatment of cancer, in particular the treatment of lung cancer, melanoma, breast cancer, prostate cancer, colon cancer, renal cell carcinoma, ovarian cancer, neuroblastoma, rhabdomyosarcoma, leukemia and lymphoma. Immunotherapeutics, generally, rely on the use of immune effector cells and molecules to target and destroy cancer cells. The effector may be a lymphocyte carrying a surface molecule that interacts, either directly or indirectly, with a tumor cell target. Various effector cells include cytotoxic T cells and NK cells. The compositions and methods described in the present invention may be utilized in conjunction with other types of therapy for cancer, such as chemotherapy, surgery, radiation, gene therapy, and so forth.

In adoptive immunotherapy, the patient's circulating lymphocytes, or tumor infiltrated lymphocytes, are isolated in vitro, activated by lymphokines such as IL-2 or transduced with genes for tumor necrosis, and readministered [Rosenberg et al., N. Engl. J. Med. 319:1767 (1988)]. To achieve this, one would administer to an animal, or human patient, an immunologically effective amount of activated lymphocytes genetically modified to express a tumor-specific chimeric receptor gene as described herein. The activated lymphocytes will most preferably be the patient's own cells that were earlier isolated from a blood or tumor sample and activated and expanded in vitro. In aspects of the present invention T lymphocytes or NK cells from a patient having a cancer of B cell origin such as lymphoblastic leukemia, B-cell chronic lymphocytic leukemia or B-cell non-Hodgkin's lymphoma would be isolated and transduced with the CD19-BB-ζ polynucleotide so that a chimeric receptor containing 4-1BB in the cytoplasmic domain is express on the cell surface of the T cell or NK cell. The modified cells would then be readministered into the patient to target and kill the tumor cells.

As shown in one Example infra, primary T-cells were transduced with the anti-CD19-BB-ζ receptor of the present invention. One week after transduction the T-cells had expanded 3-4 fold in contrast to cells that were transduced with a chimeric receptor that lacked 4-1BB. After 3 weeks in culture the T-cells had expanded by more than 16-fold.

T-cells that were transduced with the anti-CD19-BB-ζ receptor and cultured in 200 IU/mL of IL-2 for two weeks, then removed from IL-2 and exposed to irradiated OP-1 cells underwent apoptosis. However, cells cultured in 10 IU/mL of IL-2 and exposed to irradiated OP-1 cells for two weeks after transduction remained viable. T-cells that were transduced with CD19 chimeric receptors that lacked 4-1BB underwent apoptosis under these same conditions. These results show that 4-1BB co-stimulation confers a survival advantage on lymphocytes, which overcomes a major obstacle with current chimeric receptors used in immunotherapy.

To determine if T-cells transduced with the anti-CD19-BB-ζ receptor exhibited cytotoxic activity under conditions necessary for immunotherapy, their cytotoxic activity at low effector:target (E:T) ratios were measured. As described in the Example infra, T-cells transduced with the anti-CD19-BB-ζ receptor and control vectors were expanded in vitro for two weeks and mixed with OP-1 cells at various E:T ratios (1:1, 0.1:1, and 0.01:1). Viable leukemic cells were counted after one week of culture. T-cells expressing the anti-CD19-BB-ζ receptor exhibited cytotoxic activity at the 1:1 and 0.1:1 ratios against all CD19+ cell lines tested. The anti-CD19-BB-ζ receptor was not effective at the 0.01:1 ratio. The CD19 chimeric receptor that lacked 4-1BB showed cytotoxic activity at the 1:1 ratio, but at the 0.1:1 ratio the results were inferior to the anti-CD19-BB-ζ receptor.

A surprising result obtained with the anti-CD19-BB-ζ receptor was that the T-cells transduced with the receptor exhibited cytotoxic activity toward CD19+ leukemic cells at a ratio of 0.01:1 when the leukemic cells were co-cultured with bone marrow-derived mesenchymal cells. This result shows that T-cells transduced with the anti-CD19-BB-ζ receptor exhibit cytotoxic activity in an environment critical for B-lineage leukemic cell growth. Another unexpected result was that expression of the anti-CD19-BB-ζ receptor caused higher levels of TRAIL stimulation.

Furthermore, IL-2, which causes CD8+ cells to expand more vigorously, levels in cells expressing the anti-CD19-BB-ζ receptor were higher than in cells expressing the other receptors tested. These results further support the use of the anti-CD19-BB-ζ receptor for immunotherapy.

Construction of the Anti-CD19-BB-ζ Receptor

The present invention provides a chimeric receptor construct which contains the signaling domain of 4-1BB and fragments thereof. In a preferred embodiment of the invention, the genetic fragments used in the chimeric receptor were generated using splicing by overlapping extension by PCR (SOE-PCR), a technique useful for generating hybrid proteins of immunological interest. [Warrens A N, et al. Gene 20; 186: 29-35 (1997)]. Other procedures used to generate the polynucleotides and vector constructs of the present invention are well known in the art.

Transduction of T-Cells

As shown in the Examples, infra, a polynucleotide expressing a chimeric receptor capable of providing both primary effector and co-stimulatory activities was introduced into T-cells and NK cells via retroviral transduction. References describing retroviral transduction of genes are Anderson et al., U.S. Pat. No. 5,399,346; Mann et al., Cell 33:153 (1983); Temin et al., U.S. Pat. No. 4,650,764; Temin et al., U.S. Pat. No. 4,980,289; Markowitz et al., J. Virol. 62:1120 (1988); Temin et al., U.S. Pat. No. 5,124,263; International Patent Publication No. WO 95/07358, published Mar. 16, 1995, by Dougherty et al.; and Kuo et al., Blood 82:845 (1993). International Patent Publication No. WO 95/07358 describes high efficiency transduction of primary B lymphocytes.

Expansion of NK Cells

The present invention shows that human primary NK cells may be expanded in the presence of a myeloid cell line that has been genetically modified to express membrane bound IL-15 and 4-1BB ligand (CD137L). A cell line modified in this way which does not have MHC class I and II molecules is highly susceptible to NK cell lysis and activates NK cells.

For example, K562 myeloid cells can be transduced with a chimeric protein construct consisting of human IL-15 mature peptide fused to the signal peptide and transmembrane domain of human CD8α and GFP. Transduced cells can then be single-cell cloned by limiting dilution and a clone with the highest GFP expression and surface IL-15 selected. This clone can then be transduced with human CD137L, creating a K562-mb15-137L cell line.

To preferentially expand NK cells, peripheral blood mononuclear cell cultures containing NK cells are cultured with a K562-mb15-137L cell line in the presence of 10 IU/mL of IL-2 for a period of time sufficient to activate and enrich for a population of NK cells. This period can range from 2 to 20 days, preferably about 5 days. Expanded NK cells may then be transduced with the anti-CD19-BB-ζ chimeric receptor.

Administration of Activated T Cells and NK Cells

Methods of re-introducing cellular components are known in the art and include procedures such as those exemplified in U.S. Pat. Nos. 4,844,893 and 4,690,915. The amount of activated T cells or NK cells used can vary between in vitro and in vivo uses, as well as with the amount and type of the target cells. The amount administered will also vary depending on the condition of the patient and should be determined by considering all appropriate factors by the practitioner.

Obtaining an enriched population of NK cells for use in therapy has been difficult to achieve. Specific NK cell expansion has been problematic to achieve with established methods, where CD3+ T cells preferentially expand. Even after T cell depletion, residual T cells typically become prominent after stimulation. However, in accordance with the teachings of the present invention NK cells may be preferentially expanded by exposure to cells that lack or poorly express major histocompatibility complex I and/or II molecules and which have been genetically modified to express membrane bound IL-15 and 4-1BB ligand (CD137L). Such cell lines include, but are not necessarily limited to, K562 [ATCC, CCL 243; Lozzio et al., Blood 45(3): 321-334 (1975); Klein et al., Int. J. Cancer 18: 421-431 (1976)], and the Wilms tumor cell line HFWT. [Fehniger T A, Caligiuri M A. Int Rev Immunol 20(3-4):503-534 (2001); Harada H, et al., Exp Hematol 32(7):614-621 (2004)], the uterine endometrium tumor cell line HHUA, the melanoma cell line HMV-II, the hepatoblastoma cell line HuH-6, the lung small cell carcinoma cell lines Lu-130 and Lu-134-A, the neutoblastoma cell lines NB 19 and N1369, the embryonal carcinoma cell line from testis NEC 14, the cervix carcinoma cell line TCO-2, and the bone marrow-metastated neuroblastoma cell line TNB 1 [Harada H., et al., Jpn. J. Cancer Res 93: 313-319 (2002)]. Preferably the cell line used lacks or poorly expresses both MHC I and II molecules, such as the K562 and HFWT cell lines.

A solid support may be used instead of a cell line. Such supports will have attached on its surface at least one molecule capable of binding to NK cells and inducing a primary activation event and/or a proliferative response or capable of binding a molecule having such an affect thereby acting as a scaffold. The support may have attached to its surface the CD137 ligand protein, a CD137 antibody, the IL-15 protein or an IL-15 receptor antibody. Preferably, the support will have IL-15 receptor antibody and CD137 antibody bound on its surface.

The invention is intended to include the use of fragments, mutants, or variants (e.g., modified forms) of the IL-15 and/or CD137 ligand proteins or antigens that retain the ability to induce stimulation and proliferation of NK cells. A "form of the protein" is intended to mean a protein that shares a significant homology with the IL-15 or CD137 ligand proteins or antigen and is capable of effecting stimulation and proliferation of NK cells. The terms "biologically active" or "biologically active form of the protein," as used herein, are meant to include forms of the proteins or antigens that are capable of effecting enhanced activated NK cell proliferation. One skilled in the art can select such forms based on their ability to enhance NK cell activation and proliferation upon introduction of a nucleic acid encoding said proteins into a cell line. The ability of a specific form of the IL-15 or CD137 ligand protein or antigen to enhance NK cell proliferation can be readily determined, for example, by measuring cell proliferation or effector function by any known assay or method.

Antigen-specific cells can be expanded in vitro for use in adoptive cellular immunotherapy in which infusions of such cells have been shown to have anti-tumor reactivity in a tumor-bearing host. The compositions and methods of this invention can be used to generate a population of NK cells that deliver both primary and co-stimulatory signals for use in immunotherapy in the treatment of cancer, in particular the treatment of lung cancer, melanoma, breast cancer, prostate cancer, colon cancer, renal cell carcinoma, ovarian cancer, neuroblastoma, rhabdomyosarcoma, leukemia and lymphoma. The compositions and methods described in the present invention may be utilized in conjunction with other types of therapy for cancer, such as chemotherapy, surgery, radiation, gene therapy, and so forth.

9. EXAMPLES 9.1 Example 1

Introduction

In approximately 20% of children and 65% of adults with acute lymphoblastic leukemia (ALL), drug-resistant leukemic cells survive intensive chemotherapy and cause disease recurrence. [Pui C H et al, Childhood acute lymphoblastic leukemia—Current status and future perspectives. Lancet Oncology2:597-607 (2001); Verma A, Stock W. Management of adult acute lymphoblastic leukemia: moving toward a risk-adapted approach. Curr Opin Oncol 13:14-20T (2001)] lymphocyte-based cell therapy should bypass cellular mechanisms of drug resistance. Its potential clinical value for leukemia is demonstrated by the association between T-cell-mediated graft-versus-host disease (GvHD) and delay or suppression of leukemia recurrence after allogeneic stem cell transplantation. [Champlin R. T-cell depletion to prevent graft-versus-host disease after bone marrow transplantation. Hematol Oncol Clin North Am 4:687-698 (1990); Porter D L, Antin J H. The graft-versus-leukemia effects of allogeneic cell therapy. Annu Rev Med 50:369-86.:369-386 (1999); Appelbaum F R. Haematopoietic cell transplantation as immunotherapy. Nature 411:385-389 (2001)] Manipulation of GvHD by infusion of donor lymphocytes can produce a measurable anti-leukemic effect. [Porter D L, et al. Induction of graft-versus-host disease as immunotherapy for relapsed chronic myeloid leukemia. N Engl J Med 330:100-106 (1994); Kolb H J, et al. Graft-versus-leukemia effect of donor lymphocyte transfusions in marrow grafted patients. Blood 6:2041-2050 (1995); Slavin S, et al. Allogeneic cell therapy with donor peripheral blood cells and recombinant human interleukin-2 to treat leukemia relapse after allogeneic bone marrow transplantation. Blood 87:2195-2204 (1996); Collins R H, et al. Donor leukocyte infusions in 140 patients with relapsed malignancy after allogeneic bone marrow transplantation. J Clin Oncol 15:433-444 (1997)] However, in patients with ALL this effect is often limited, [Kolb H J, et al. Graft-versus-leukemia effect of donor lymphocyte transfusions in marrow grafted patients. Blood 86:2041-2050 (1995); Verdonck L F, et al. Donor leukocyte infusions for recurrent hematologic malignancies after allogeneic bone marrow transplantation: impact of infused and residual donor T cells. Bone Marrow Transplant 22:1057-1063 (1998); Collins R H, Jr., et al. Donor leukocyte infusions in acute lymphocytic leukemia. Bone Marrow Transplant 26:511-516 (2000)] possibly reflecting inadequate T-cell stimulation by leukemic lymphoblasts.

T lymphocyte specificity can be redirected through expression of chimeric immune receptors consisting of an extracellular antibody-derived single-chain variable domain (scFv) and an intracellular signal transduction molecule (e.g., the signaling domain of CD3ζ or FcγRIII). [Geiger T L, Jyothi M D. Development and application of receptor-modified T lymphocytes for adoptive immunotherapy. Transfus Med Rev 15:21-34 (2001); Schumacher T N. T-cell-receptor gene therapy. Nat Rev Immunol. 2:512-519 (2002); Sadelain M, et al. Targeting tumours with genetically enhanced T lymphocytes. Nat Rev Cancer 3:35-45 (2003)] Such T lymphocytes can be activated by cell surface epitopes targeted by the scFv and can kill the epitope-presenting cells. The first requirement to redirect T cells against ALL cells is the identification of target molecules that are selectively expressed by leukemic cells. In B-lineage ALL, CD19 is an attractive target, because it is expressed on virtually all leukemic lymphoblasts in almost all cases. [Campana D, Behm F G. Immunophenotyping of leukemia. J Immunol Methods 243:59-75 (2000)] It is not expressed by normal non-hematopoietic tissues, and among hematopoietic cells, it is expressed only by B-lineage lymphoid cells. [Campana D, Behm F G. Immunophenotyping of leukemia. J Immunol Methods 243:59-75 (2000); Nadler L M, et al. B4, a human B lymphocyte-associated antigen expressed on normal, mitogen-activated, and malignant B lymphocytes. J Immunol 131:244-250 (1983)] Recent studies have shown that T-cells expressing anti-CD19 scFv and CD3ζ signaling domain can proliferate when mixed with CD19$^+$ cells and can lyse CD19$^+$ target cells. [Cooper L J, et al. T-cell clones can be rendered specific for CD19: toward the selective augmentation of the graft-versus-B-lineage leukemia effect. Blood 101:1637-1644 (2003); Brentjens R J, et al. Eradication of systemic B-cell tumors by genetically targeted human T lymphocytes co-stimulated by CD80 and interleukin-15. Nat Med 9:279-286 (2003)]

A prerequisite for the success of T-cell therapy is the capacity of the engineered T lymphocytes to expand and produce a vigorous and durable anti-leukemic response in vivo. The engagement of the TCR, although necessary, is not sufficient to fully activate T cells; a second signal, or co-stimulus, is also required. [Liebowitz D N, et al. Costimulatory approaches to adoptive immunotherapy. Curr Opin Oncol 10:533-541 (1998); Allison J P, Lanier L L. Structure, function, and serology of the T-cell antigen receptor complex. Annu Rev Immunol 5:503-540 (1987); Salomon B, Bluestone J A. Complexities of CD28/B7: CTLA-4 costimulatory pathways in autoimmunity and transplantation. Annu Rev Immunol 19:225-52.:225-252 (2001)] This could be a major obstacle for chimeric receptor-based therapy of B-lineage ALL, because B-lineage leukemic lymphoblasts generally lack B7 molecules that bind to CD28 on T-lymphocytes and trigger the CD28-mediated co-stimulatory pathway. [Cardoso A A, et al. Pre-B acute lymphoblastic leukemia cells may induce T-cell anergy to alloantigen. Blood 88:41-48 (1996)] This limitation might be overcome by incorporating the signal transduction domain of CD28 into chimeric receptors. [Eshhar Z, et al. Functional expression of chimeric receptor genes in human T cells. J Immunol Methods 2001; 248:67-76 (2001); Hombach A, et al. Tumor-specific T cell activation by recombinant immunoreceptors: CD3 zeta signaling and CD28 costimulation are simultaneously required for efficient IL-2 secretion and can be integrated into one combined CD28/CD3 zeta signaling receptor molecule. J Immunol 167: 6123-6131 (2001); Geiger T L, et al. Integrated src kinase and costimulatory activity enhances signal transduction through single-chain chimeric receptors in T lymphocytes. Blood 98:2364-2371 (2001); Maher J, et al. Human T-lymphocyte cytotoxicity and proliferation directed by a single chimeric TCRzeta/CD28 receptor. Nat Biotechnol 20:70-75 (2002)] Murine T cells bearing such receptors have shown a greater capacity to inhibit cancer cell growth and metastasis in mice than those with chimeric receptors lacking this domain. [Haynes N M, et al. Rejection of syngeneic colon carcinoma by CTLs expressing single-chain antibody receptors codelivering CD28 costimulation. J Immunol 169:5780-5786 (2002); Haynes N M, et al. Single-chain antigen recognition receptors that costimulate potent rejection of established experimental tumors. Blood 100:3155-3163 (2002)]

A second co-stimulatory pathway in T cells, independent of CD28 signaling, is mediated by 4-1BB (CD137), a member of the tumor necrosis factor (TNF) receptor family. [Sica G, Chen L. Modulation of the immune response through 4-1BB. In: Habib N, ed. Cancer gene therapy: past achievements and future challenges. New York: Kluwer Academic/Plenum Publishers; 355-362 (2000)] 4-1BB stimulation significantly enhances survival and clonal expansion of CD8+ T-lymphocytes, and CD8+ T-cell responses in a variety of settings, including viral infection, allograft rejection, and tumor immunity. [Shuford W W, et al. 4-1BB costimulatory signals preferentially induce CD8+ T cell proliferation and lead to the amplification in vivo of cytotoxic T cell responses. J Exp Med 186:47-55 (1997); Melero I, et al. Monoclonal antibodies against the 4-1BB T-cell activation molecule eradicate established tumors. Nat Med 3:682-685 (1997); Melero I, et al. Amplification of tumor immunity by gene transfer of the co-stimulatory 4-1BB ligand: synergy with the CD28 co-stimulatory pathway. Eur J Immunol 28:1116-1121 (1998); Takahashi C, et al. Cutting edge: 4-1BB is a bona fide CD8 T cell survival signal. J Immunol 162:5037-5040 (1999); Martinet O, et al. T cell activation with systemic agonistic antibody versus local 4-1BB ligand gene delivery combined with interleukin-12 eradicate liver metastases of breast cancer. Gene Ther 9:786-792 (2002); May K F, Jr., et al. Anti-4-1BB monoclonal antibody enhances rejection of large tumor burden by promoting survival but not clonal expansion of tumor-specific CD8+ T cells. Cancer Res 62:3459-3465 (2002)] However, the natural ligand of 4-1BB is weakly and heterogeneously expressed in B-lineage ALL cells (C. Imai, D. Campana, unpublished observations). Therefore, it is likely that this important co-stimulatory signal, like CD28, can become operational only if 4-1BB is added to chimeric receptors. However, it is not known whether such receptors would help deliver effective T-cell responses to cancer cells and, if so, whether these would be equivalent to those elicited by receptors containing CD28.

We constructed a chimeric T-cell receptor specific for CD19 that contains a 4-1BB signaling domain. We determined whether T cells transduced with these receptors could effectively destroy B-lineage ALL cell lines and primary leukemic cells under culture conditions that approximate the in vivo microenvironment where leukemic cells grow. We compared the properties of T-cells expressing the 4-1BB-containing receptor to those of T-cells expressing an equivalent receptor lacking 4-1BB or containing CD28 instead.

Materials and Methods

Cells

Available in our laboratory were the human B-lineage ALL cell line OP-1, developed from the primary leukemic cells of a patient with newly diagnosed B-lineage ALL with the t(9; 22)(q34;q11) karyotype and the BCR-ABL gene fusion; [Manabe A, et al. Interleukin-4 induces programmed cell death (apoptosis) in cases of high-risk acute lymphoblastic leukemia. Blood 83:1731-1737 (1994)] the B-lineage ALL cell lines RS4;11, [Stong R C, et al. Human acute leukemia cell line with the t(4;11) chromosomal rearrangement exhibits B lineage and monocytic characteristics. Blood 1985; 65:21-31 (1985)] and REH [Rosenfeld C, et al. Phenotypic characterisation of a unique non-T, non-B acute lymphoblastic leukaemia cell line. Nature 267:841-843 (1977)]; the T-cell lines Jurkat [Schneider U, et al. Characterization of EBV-genome negative "null" and "T" cell lines derived from children with acute lymphoblastic leukemia and leukemic transformed non-Hodgkin lymphoma. Int J Cancer 1977; 19:621-626 (1977)] and CEM-C7 [Harmon J M, et al. Dexamethasone induces irreversible G1 arrest and death of a human lymphoid cell line. J Cell Physiol 98:267-278 (1979)]; and the myeloid cell lines K562 [Koeffler H P, Golde D W. Acute myelogenous leukemia: a human cell line responsive to colony-stimulating activity. Science 200:1153-1154 (1978)] and U-937. [Sundstrom C, Nilsson K. Establishment and characterization of a human histiocytic lymphoma cell line (U-937). Int J Cancer 1976; 17:565-577 (1976)] Cells were maintained in RPMI-1640 (Gibco, Grand Island, N.Y.) with 10% fetal calf serum (FCS; BioWhittaker, Walkersville, Md.) and antibiotics. Human adenocarcinoma HeLa cells and embryonic kidney fibroblast 293T cells, maintained in DMEM (MediaTech, Herndon, Va.) supplemented with 10% FCS and antibiotics, were also used.

We used primary leukemia cells obtained from 5 patients with newly diagnosed B-lineage ALL with the approval of the St. Jude Children's Research Hospital Institutional Review Board and with appropriate informed consent. The diagnosis of B-lineage ALL was unequivocal by morphologic, cytochemical, and immunophenotypic criteria; in each case, more than 95% of leukemic cells were positive for CD19. Peripheral blood samples were obtained from 7 healthy adult donors. Mononuclear cells were collected from the samples by centrifugation on a Lymphoprep density step (Nycomed, Oslo, Norway) and were washed two times in phosphate-buffered saline (PBS) and once in AIM-V medium (Gibco).

Plasmids

The plasmid encoding anti-CD19 scFv was obtained from Dr. I. Nicholson (Child Health Research Institute, Adelaide, Australia). [Nicholson I C, et al. Construction and characterisation of a functional CD19 specific single chain Fv fragment for immunotherapy of B lineage leukaemia and lymphoma. Mol Immunol 34:1157-1165 (1997)] The pMSCV-IRES-GFP, pEQPAM3(-E), and pRDF were obtained from Dr. E. Vanin at our institution. Signal peptide, hinge and transmembrane domain of CD8α, and intracellular domains of 4-1BB, CD28, CD3ζ and CD19 were subcloned by polymerase chain reaction (PCR) using a human spleen cDNA library (from Dr. G. Neale, St. Jude Children's Research Hospital) as a template. FIG. 1 shows a schematic representation of the anti-CD19-ζ, anti-CD19-BB-ζ anti-CD19-28-sand anti-CD19-truncated (control) constructs. We used splicing by overlapping extension by PCR (SOE-PCR) to assemble several genetic fragments. [Warrens A N, et al. Splicing by overlap extension by PCR using asymmetric amplification: an improved technique for the generation of hybrid proteins of immunological interest. Gene 20; 186:29-35 (1997)] The sequence of each genetic fragment was confirmed by direct sequencing. The resulting expression cassettes were subcloned into EcoRI and XhoI sites of MSCV-IRES-GFP.

To transduce CD19-negative K562 cells with CD19, we constructed a MSCV-IRES-DsRed vector. The IRES and DsRed sequences were subcloned from MSCV-IRES-GFP and pDsRedN1 (Clontech, Palo Alto, Calif.), respectively, and assembled by SOE-PCR. The IRES-DsRed cassette was digested and ligated into XhoI and NotI sites of MSCV-IRES-GFP. The expression cassette for CD19 was subsequently ligated into EcoRI and XhoI sites of MSCV-IRES-DsRed vector.

Virus Production and Gene Transduction

To generate RD114-pseudotyped retrovirus, we used calcium phosphate DNA precipitation to transfect $3 \times 10^6$ 293T cells, maintained in 10-cm tissue culture dishes (Falcon, Becton Dickinson, Franklin Lakes, N.J.) for 24 hours, with 8 µg of one of the vectors anti-CD19-ζ, anti-CD19-BB-ζ, anti-CD19-28-ζ0 or anti-CD19-truncated, 8 µg of pEQ-PAM3(-E) and 4 µg of pRDF. After 24 hours, medium was replaced with RPMI-1640 with 10% FCS and antibiotics. Conditioned medium containing retrovirus was harvested 48 hours and 72 hours after transfection, immediately frozen in dry ice, and stored at −80° C. until use. HeLa cells were used to titrate virus concentration.

Peripheral blood mononuclear cells were incubated in a tissue culture dish for 2 hours to remove adherent cells. Non-adherent cells were collected and prestimulated for 48 hours with 7 µg/mL PHA-M (Sigma, St. Louis, Mo.) and 200 IU/mL human IL-2 (National Cancer Institute BRB Preclinical Repository, Rockville, Md.) in RPMI-1640 and 10% FCS. Cells were then transduced as follows. A 14-mL polypropylene centrifuge tube (Falcon) was coated with 0.5 mL of human fibronectin (Sigma) diluted to 100 µg/mL for 2 hours at room temperature and then incubated with 2% bovine serum albumin (Sigma) for 30 minutes. Prestimulated cells ($2 \times 10^5$) were resuspended in the fibronectin-coated tube in 2-3 mL of virus-conditioned medium with polybrene (4 µg/mL; Sigma) and centrifuged at 2400×g for 2 hours. The multiplicity of infection (4 to 8) was identical in each experiment comparing the activity of different chimeric receptors. After centrifugation, cells were left undisturbed for 24 hours in a humidified incubator at 37° C., 5% $CO_2$. The transduction procedure was repeated on two successive days. Cells were then washed twice with RPMI-1640 and maintained in RPMI-1640, 10% FCS, and 200 IU/mL of IL-2 until use.

A similar procedure was used to express chimeric receptors in Jurkat cells, except that cells were not prestimulated. K562 cells expressing CD19 were created by resuspending $2 \times 10^5$ K562 cells in 3 mL of MSCV-CD19-IRES-DsRed virus medium with 4 µg/mL polybrene in a fibronectin-coated tube; the tube was centrifuged at 2400×g for 2 hours and left undisturbed in an incubator for 24 hours. Control cells were transduced with the vector only. These procedures were repeated on 3 successive days. After confirming CD19 and DsRed expression, cells were subjected to single-cell sorting with a fluorescence-activated cell sorter (MoFlo, Cytomation, Fort Collins, Colo.). The clones that showed the highest expression of DsRed and CD19 and of DsRed alone were selected for further experiments.

Detection of Chimeric Receptor Expression

Transduced Jurkat and peripheral blood cells were stained with goat anti-mouse (Fab)2 polyclonal antibody conjugated with biotin (Jackson Immunoresearch, West Grove, Pa.) followed by streptavidin conjugated to peridinin chlorophyll protein (PerCP; Becton Dickinson, San Jose, Calif.). Patterns of CD4, CD8, and CD28 expression were also analyzed by using anti-CD4 and anti-CD28 conjugated to PE and anti-CD8 conjugated to PerCP (antibodies from Becton Dickinson, and Pharmingen, San Diego, Calif.). Antibody staining was detected with a FACScan flow cytometer (Becton Dickinson).

For Western blotting, $2 \times 10^7$ cells were lysed in 1 mL RIPA buffer (PBS, 1% Triton-X100, 0.5% sodium deoxycholate, 0.1% SDS) containing 3 μg/mL of pepstatin, 3 μg/mL of leupeptin, 1 mM of PMSF, 2 mM of EDTA, and 5 μg/mL of aprotinin. Centrifuged lysate supernatants were boiled with an equal volume of loading buffer with or without 0.1 M DTT, then were separated by SDS-PAGE on a precast 12% acrylamide gel (BioRad, Hercules, Calif.). The proteins were transferred to a PVDF membrane, which was incubated with primary mouse anti-human CD3ζ monoclonal antibody (clone 8D3; Pharmingen), 1 μg/mL for 12 hours at 4° C. Membranes were then washed, incubated with a 1:500 dilution of goat anti-mouse IgG horseradish peroxidase-conjugated second antibody for 1 hour, and developed by using the ECP kit (Pharmacia, Piscataway, N.J.).

Changes in Gene Expression and Cytokine Production after Receptor Ligation

Jurkat cells transduced with the chimeric receptors were cocultured with OP-1 leukemic cells fixed with 0.5% paraformaldehyde at an effector:target (E:T) ratio of 1:1. RNA was extracted using Trizol Reagent (Invitrogen, Carlsbad, Calif.). Gene expression of Jurkat cells was analyzed using HG-U133A GeneChip microarrays (Affymetrix, Santa Clara, Calif.) as previously described. [Yeoh E J, et al. Classification, subtype discovery, and prediction of outcome in pediatric acute lymphoblastic leukemia by gene expression profiling. Cancer Cell 2002; 1:133-143 (2002); Ross M E, et al. Classification of pediatric acute lymphoblastic leukemia by gene expression profiling. Blood. May 2003; 10.1182/blood-2003-01-0338 (2003)] Arrays were scanned using a laser confocal scanner (Agilent, Palo Alto, Calif.) and analyzed with Affymetrix Microarray suite 5.0. We used an arbitrary factor of 2 or higher to define gene overexpression. IL-2, TNF-related apoptosis-inducing ligand (TRAIL), OX40, IL-3 and μ-actin transcripts were detected by semi-quantitative reverse transcriptase-polymerase chain reaction (RT-PCR) using Jurkat cells stimulated as above; primers were designed using the Primer3 software developed by the Whitehead Institute for Biomedical Research.

For cytokine production, Jurkat cells and primary lymphocytes ($2 \times 10^5$ in 200 μl) expressing chimeric receptors were stimulated with OP-1 cells at a 1:1 E:T ratio for 24 hours. Levels of IL-2 and IFNγ in culture supernatants were determined with a Bio-Plex assay (BioRad). Lymphocytes before and after stimulation were also labeled with anti-TRAIL-PE (Becton Dickinson).

Expansion and Purification of Receptor-Transduced Primary T Cells

Receptor-transduced lymphocytes ($3 \times 10^5$) were co-cultured with $1.5 \times 10^5$ irradiated OP-1 cells in RPMI-1640 with 10% FCS with or without exogenous IL-2. Cells were pulsed weekly with irradiated target cells at an E:T ratio of 2:1. Cells were counted by Trypan-blue dye exclusion and by flow cytometry to confirm the presence of GFP-positive cells and the absence of CD19-positive cells. To prepare pure populations of CD8+ cells expressing chimeric receptors, we labeled cells with a PE-conjugated anti-CD8 antibody (Becton Dickinson) that had been previously dialyzed to remove preservatives and then sterile-filtered. CD8+ GFP+ cells were isolated using a fluorescence-activated cell sorter (MoFlo).

Cytotoxicity Assays

The cytolytic activity of transductants was measured by assays of lactate dehydrogenase (LDH) release using the Cytotoxicity Detection Kit (Roche, Indianapolis, Ind.) according to the manufacturer's instructions. Briefly, $2 \times 10^4$ target cells were placed in 96-well V-bottom tissue culture plates (Costar, Cambridge, Mass.) and cocultured in triplicate in RPMI-1640 supplemented with 1% FCS, with primary lymphocytes transduced with chimeric receptors. After 5 hours, cell-free supernatant was harvested and immediately analyzed for LDH activity. Percent specific cytolysis was calculated by using the formula: (Test—effector control—low control/high control—low control)×100, in which "high control" is the value obtained from supernatant of target cells exposed to 1% Triton-X-100, "effector control" is the spontaneous LDH release value of lymphocytes alone, "low control" is the spontaneous LDH release value of target cells alone; background control (the value obtained from medium alone) was subtracted from each value before the calculation.

The anti-leukemic activity of receptor-transduced lymphocytes was also assessed in 7-day cultures using lower E:T ratios. For this purpose, we used bone marrow-derived mesenchymal cells to support the viability of leukemic cells. [Nishigaki H, et al. Prevalence and growth characteristics of malignant stem cells in B-lineage acute lymphoblastic leukemia. Blood 89:3735-3744 (1997); Mihara K, et al. Development and functional characterization of human bone marrow mesenchymal cells immortalized by enforced expression of telomerase. Br J Haematol 120:846-849 (2003)] Briefly, $2 \times 10^4$ human mesenchymal cells immortalized by enforced expression of telomerase reverse transcriptase were plated on a 96-well tissue culture plate precoated with 1% gelatin. After 5 days, $1 \times 10^4$ CD19+ target cells (in case of cell lines) or $2 \times 10^5$ CD19+ target cells (in case of primary ALL cells) were plated on the wells and allowed to rest for 2 hours. After extensive washing to remove residual IL-2-containing medium, receptor-transduced primary T cells were added to the wells at the proportion indicated in Results. Cultures were performed in the absence of exogenous IL-2. Plates were incubated at 37° C. in 5% $CO_2$ for 5-7 days. Cells were harvested, passed through a 19-gauge needle to disrupt residual mesenchymal-cell aggregates, stained with anti-CD19-PE antibody, and assayed by flow cytometry as previously described. [Ito C, et al. Hyperdiploid acute lymphoblastic leukemia with 51 to 65 chromosomes: A distinct biological entity with a marked propensity to undergo apoptosis. Blood 93:315-320 (1999); Srivannaboon K, et al. Interleukin-4 variant (BAY 36-1677) selectively induces apoptosis in acute lymphoblastic leukemia cells. Blood 97:752-758 (2001)] Expression of DsRed served as a marker of residual K562 cells. Experiments were done in triplicate.

Results

Transduction of Primary Human T Lymphocytes with Anti-CD19-BB-ζ Chimeric Receptors In preliminary experiments, transduction of lymphocytes stimulated with PHA (7 μg/mL) and IL-2 (200 IU/mL) for 48 hours, followed by centrifugation (at 2400×g) of the activated lymphocytes with retroviral supernatant in tubes coated with fibronectin, consistently yielded a high percentage of chimeric receptor and GFP expression; this method was used in all subsequent experiments. In 75 transduction experiments, 31% to 86% (median, 64%) of mononuclear cells expressed GFP. In experiments with cells obtained from 6 donors, we tested the immunophenotype of the cells transduced with anti-CD19-BB-ζ receptors. Fourteen days after transduction a mean (±SD) of 89.6%±2.3% (n=6) of GFP cells also expressed CD3; 66.2%±17.9% of CD3 T lymphocytes were transduced. Among GFP+ cells, 21.1%±8.8% (n=6) were CD4+, 68.1%±8.1% (n=6) were CD8+, 38.1%±16.1% (n=3) were CD28+ and 24.2%±11.6% (n=3) were CD8+CD28+. These proportions were similar to those obtained with the anti-CD19-ζ receptors lacking 4-1BB. In this case, 85.4%±11.0% (n=6) of GFP+ cells expressed CD3; 60.8%±10.1% of CD3+ cells were transduced. Among GFP+ cells, 18.0%±8.7% (n=6) were CD4+, 66.1%±11.7% (n=6) were CD8+, 41.2%±12.2% (n=3) were CD28+ and 20.6%±11.3% (n=3) were CD8+CD28+. In these experiments, median transduction efficiency was 65% (range, 31% to 86%) for anti-CD19-BB-ζ receptors, and 65% (range, 37% to 83%) for anti-CD19-ζ receptors.

The surface expression of the chimeric receptors on GFP+ cells was confirmed by staining with a goat anti-mouse antibody that reacted with the scFv portion of anti-CD19. Expression was detectable on most GFP+ cells and was not detectable on GFP cells and vector-transduced cells. The level of surface expression of anti-CD19-BB-ζ was identical to that of the receptor lacking 4-1BB. Expression was confirmed by Western blot analysis; under non-reducing conditions, peripheral blood mononuclear cells transduced with the chimeric receptors expressed them mostly as monomers, although dimers could be detected.

Signaling Function of Anti-CD19-BB-ζ Chimeric Receptors

To test the functionality of the anti-CD19-BB-ζ chimeric receptor, we used the T-cell line Jurkat and the CD19+ ALL cell line OP-1. After transduction, >95% Jurkat cells were GFP+. Exposure of irradiated OP-1 cells to Jurkat cells transduced with anti-CD19-BB-ζ triggered transcription of IL-2. Notably, in parallel experiments with Jurkat cells transduced with the anti-CD19-ζ receptor lacking 4-1BB, the level of IL-2 transcription was much lower. No IL-2 transcription was detected in Jurkat cells transduced with the anti-CD19-truncated control receptor lacking CD3ζ.

To identify further changes in molecules associated with T-cell activation, survival or cytotoxicity induced by anti-CD19-BB-ζ receptors, Jurkat cells were either transduced with these receptors or with anti-CD19-ζ receptors and then stimulated with paraformadehyde-fixed OP-1 cells. After 12 hours of stimulation, we screened the cells' gene expression using Affymetrix HG-U133A chips. Genes that were overexpressed by a factor of 2 or higher in cells with anti-CD19-BB-ζ included the member of the TNF family TRAIL, the TNF-receptor member OX40, and IL-3. Overexpression of these molecules after stimulation was validated using RT-PCR. In cells bearing the anti-CD19-ζ receptor, there were no overexpressed genes with a known function associated with T-cells. Therefore, anti-CD19-BB-ζ receptors elicit transcriptional responses that are distinct from those triggered by receptors lacking 4-1BB.

Expansion of T Cells Expressing Anti-CD19-BB-ζ Receptors in the Presence of CD19+ Cells To measure the ability of anti-CD19-BB-ζ transduced lymphocytes to survive and expand in vitro, we first analyzed primary T cells (obtained from 2 donors), 7 days after transduction. Transduction efficiency with the 3 receptors was similar: 72% and 67% for anti-CD19-BB-ζ, 63% and 66% for anti-CD19-ζ and 67% and 68% for the truncated anti-CD19 receptor. When cocultured with irradiated OP-1 ALL cells in the absence of exogenous IL-2, cells transduced with anti-CD19-BB-ζ expanded: after only 1 week of culture, GFP+ cells recovered were 320% and 413% of input cells. T cells that expressed the anti-CD19-ζ receptor but lacked 4-1BB signaling capacity remained viable but showed little expansion (cell recovery: 111% and 160% of input cells, respectively), whereas those that expressed the truncated anti-CD19 receptor underwent apoptosis (<10% of input cells were viable after 1 week). Lymphocytes transduced with anti-CD19-BB-ζ continued to expand in the presence of irradiated OP-1 cells. After 3 weeks of culture, they had expanded by more than 16-fold, with 98% of the cells at this point being GFP+. By contrast, cells transduced with only anti-CD19-ζ survived for less than 2 weeks of culture.

We performed the next set of experiments with T cells (obtained from 3 donors) 14 days after transduction with anti-CD19-BB-ζ, anti-CD19-ζ or anti-CD19-truncated, and expanded with high-dose IL-2 (200 IU/mL). Recovery of lymphocytes of each donor with anti-CD19-BB-ζ receptors was significantly higher than that of lymphocytes with anti-CD19-ζ receptors in all 3 comparisons (P<0.005). When IL-2 was removed, exposure of the transduced cells to irradiated OP-1 cells induced apoptosis, irrespective of the chimeric receptor expressed. This was in contrast to results with cells 7 days post-transduction, and in accord with the loss of T cell functionality after prolonged culture in IL-2 observed by others. [Brentjens R J, et al. Eradication of systemic B-cell tumors by genetically targeted human T lymphocytes co-stimulated by CD80 and interleukin-15. Nat Med 9:279-286 (2003); Rossig C. et al. Targeting of G(D2)-positive tumor cells by human T lymphocytes engineered to express chimeric T-cell receptor genes. Int J Cancer 94:228-236 (2001)] However, low-dose IL-2 (10 IU/mL) was sufficient to maintain most lymphocytes transduced with anti-CD19-BB-ζ viable after 2 weeks of culture with irradiated OP-1 cells, but did not prevent apoptosis of cells transduced with the other receptors. Taken together, these data indicate that 4-1BB-mediated costimulation confers a survival advantage on lymphocytes.

Cytotoxicity Triggered by Anti-CD19-BB-ζ Chimeric Receptors

Lymphocytes obtained from two donors and transduced with anti-CD19-BB-ζ and anti-CD19-ζ exerted dose-dependent cytotoxicity, as shown by a 5-hour LDH release assay using the OP-1 B-lineage ALL cell line as a target. Transduction efficiencies were 41% and 73% for empty vector, 40% and 67% for anti-CD19-truncated, 43% and 63% for anti-CD19-ζ, and 46% and 72% for anti-CD19-BB-ζ. No differences in cytotoxicities mediated by the two receptors were detectable with this assay. Although no lysis of target cells was apparent at a 1:1 ratio in the 5-hour LDH assay, most leukemic cells were specifically killed by lymphocytes expressing signaling chimeric receptors when the cultures were examined at 16 hours by flow cytometry and inverted microscopy.

To better mimic the application of T-cell therapy, we determined whether T cells expressing the chimeric receptor would exert significant anti-leukemic activity when present at low E:T ratios in prolonged culture. Lymphocytes from various donors were expanded in vitro for 14 days after transduction and were mixed at different ratios with OP-1, RS4;11, or REH B-lineage ALL cells, or with K562 (a CD19-negative myeloid cell line that lacks HLA antigens) transduced with CD19 or with vector alone. Co-cultures were maintained for 7 days, and viable leukemic cells were counted by flow cytometry. As observed in short term cultures, at a 1:1 ratio, T cells expressing signaling chimeric receptors eliminated virtually all leukemic cells from the cultures. At a 0.1:1 ratio, however, T cells transduced with anti-CD19-BB-ζ receptors were markedly more effective than those lacking 4-1BB signaling. Chimeric receptor-transduced T cells had no effect on cells lacking CD19. The presence of 4-1BB in the chimeric receptor did not increase background, non-CD19-mediated cytotoxicity, in experiments using CEM-C7, U-937 and K-562. As in other experiments, transduction efficiencies with the two chimeric receptors were equivalent, and range from 62% to 73% for anti-CD19-ζ and from 60% to 70% for anti-CD19-BB-ζ.

Cells present in the bone marrow microenvironment may decrease T-cell proliferation in a mixed lymphocyte reaction. [Bartholomew A, et al. Mesenchymal stem cells suppress lymphocyte proliferation in vitro and prolong skin graft survival in vivo. Exp Hematol 30:42-48 (2002); Krampera M, et al. Bone marrow mesenchymal stem cells inhibit the response of naive and memory antigen-specific T cells to their cognate peptide. Blood 101:3722-3729 (2003); Le Blanc K, et al. Mesenchymal stem cells inhibit and stimulate mixed lymphocyte cultures and mitogenic responses independently of the major histocompatibility complex. Scand J Immunol 57:11-20 (2003)] To test whether these cells would also affect T-cell-mediated antileukemic activity, we repeated the experiments with OP-1 in the presence of bone marrow-derived mesenchymal cell layers. [Mihara K, et al. Development and functional characterization of human bone marrow mesenchymal cells immortalized by enforced expression of telomerase. Br J Haematol 2003; 120:846-849 (2003)] T-cell cytotoxicity under these conditions was even greater than that observed in cultures without mesenchymal cells. Remarkably, T cells transduced with anti-CD19-BB-ζ were markedly cytotoxic even at a ratio of 0.01:1 in this assay, whereas those transduced with anti-CD19-ζ were not.

Effect of Receptor-Transduced T Cells on Primary Leukemic Cells

We co-cultured primary B-lineage ALL cells with bone marrow-derived mesenchymal cells, which are essential to preserve their viability in vitro. [Nishigaki H, et al. Prevalence and growth characteristics of malignant stem cells in B-lineage acute lymphoblastic leukemia. Blood 1997; 89:3735-3744 (1997); Mihara K, et al. Development and functional characterization of human bone marrow mesenchymal cells immortalized by enforced expression of telomerase. Br J Haematol 120:846-849 (2003)] We tested the effect of T cells expressing anti-CD19-BB-ζ on primary leukemic cells obtained from 5 patients at the time of diagnosis; these patients included 3 who had B-lineage ALL with 11q23 abnormalities, a karyotype associated with drug resistance. [Pui C H, et al. Childhood acute lymphoblastic leukemia—Current status and future perspectives. Lancet Oncology 2:597-607 (2001)] Mesenchymal cells supported ALL cell survival in vitro: in cultures not exposed to exogenous T cells, recovery of leukemic cells from the 5 patients after 5 days of culture ranged from 100.1% to 180.7% of the input cell number. Leukemic cells incubated at a 0.1:1 ratio with lymphocytes expressing anti-CD19-BB-ζ were virtually eliminated in all 5 cultures. Remarkable cytotoxicity was also seen at a 0.01:1 ratio. Importantly, at this ratio, lymphocytes expressing anti-CD19-BB-ζ were consistently more cytotoxic than those expressing the anti-CD19-ζ receptor alone (P<0.01 by t test for all comparisons).

Comparisons Between Chimeric Receptors Containing Signaling Domains of 4-1BB and of CD28

We compared responses induced by anti-CD19-BB-ζ to those of an equivalent receptor in which 4-1BB signaling domains were replaced by CD28 signaling domains (FIG. 1). Expression of the latter was similar to that of anti-CD19-BB-ζ and anti-CD19-ζ receptors: >95% Jurkat cells were consistently GFP+ after transduction with anti-CD19-28-ζ and most of these cells had detectable receptors on the cell surface. In 6 experiments with primary lymphocytes, transduced cells ranged from 42% to 84% (median, 72%).

We tested production of IL-2 in Jurkat cells transduced with the three receptors and stimulated with the CD19+ ALL cell line OP-1. Production of IL-2 was the highest in cells expressing anti-CD19-BB-ζ (P<0.05). Production of IL-2 was also tested in primary lymphocytes, which were transduced with the chimeric receptors and then expanded for 5 weeks with pulses of OP-1. The pattern of IL-2 production was similar to that observed in Jurkat cells. Cells expressing anti-CD19-BB-ζ produced higher levels of IL-2 (P<0.01). Chimeric receptors containing the co-stimulatory molecules induced a higher IFN-γ production in primary lymphocytes. IFN-γ levels were the highest with the anti-CD19-28-ζ receptor (P<0.05). Finally, we tested surface expression of TRAIL protein in primary lymphocytes by staining with a specific antibody. Levels of TRAIL were the highest in cells transduced with the anti-CD19-BB-ζ receptor. These results indicate that anti-CD19-BB-ζ receptors are functionally distinct from those lacking co-stimulatory molecules or containing CD28 instead of 4-1BB.

Next, we compared the cytotoxicity exerted by primary T cells transduced with anti-CD19-BB-ζ receptors to those exerted by T cells bearing receptors lacking 4-1BB. For these experiments, we transduced primary lymphocytes from 2 donors with anti-CD19-BB-ζ anti-CD19-28-ζ, anti-CD19-ζ and anti-CD19-truncated, we expanded them for 2-3 weeks with IL-2, and then purified CD8+, GFP+ cells by fluorescence activated cell sorting. Confirming our previous results with unsorted cells, CD8+ cells expressing anti-CD19-BB-ζ receptors were significantly more effective than those with anti-CD19-ζ receptors, and were as effective as those with anti-CD19-BB-ζ Finally, we determined the capacity of the purified CD8 cells transduced with the various receptors to expand in the presence of low dose (10 U/mL) IL-2. Cells transduced with anti-CD19-BB-ζ receptor had a significantly higher cell growth under these conditions than those bearing the other receptors (P<0.001).

Discussion

Results of this study indicate that anti-CD19-BB-ζ receptors could help achieve effective T-cell immunotherapy of B-lineage ALL. Lymphocytes expressing anti-CD19-BB-ζ survived and expanded better than those with equivalent receptors lacking 4-1BB. These lymphocytes also had higher anti-leukemic activity and could kill B-lineage ALL cells from patients at E:T ratios as low as 0.01:1, suggesting that the infusion of relatively low numbers of transduced T cells could have a measurable anti-leukemic effect in patients. Finally, lymphocytes transduced with anti-CD19-BB-ζ were particularly effective in the presence of bone marrow-derived mesenchymal cells which form the microenvironment critical for B-lineage ALL cell growth, further supporting their potential for immunotherapy.

Two recently reported studies used anti-CD19 scFv as a component of a chimeric receptor for T-cell therapy of B-cell malignancies. Cooper et al. Blood 101:1637-1644 (2003) reported that T-cell clones transduced with chimeric receptors comprising anti-CD19 scFv and CD3ζ produced approximately 80% specific lysis of B-cell leukemia and lymphoma cell lines at a 1:1 E:T ratio in a 4-hour $^{51}$Cr release assay; at this ratio, percent specific lysis of one primary B-lineage ALL sample tested was approximately 30%. Brentjens et al. Nat Med 279-286 (2003) reported that T-cells bearing anti-CD19 scFv and CD3ζ chimeric receptors could be greatly expanded in the presence of exogenous IL-15 and artificial antigen-presenting cells transduced with CD19 and CD80. The authors showed that these T cells significantly improved the survival of immunodeficient mice engrafted with the Raji B-cell lymphoma cell line. Their results demonstrated the requirement for co-stimulation in maximizing T-cell-mediated anti-leukemic activity: only cells expressing the B7 ligands of CD28 elicited effective T-cell responses. However, B-lineage ALL cells typically do not express B7-1(CD80) and only a subset expresses B7-2 (CD86) molecules. [Cardoso A A, et al. Pre-B acute lymphoblastic leukemia cells may induce T-cell anergy to alloantigen. Blood 88:41-48 (1996)]

4-1BB, a tumor necrosis factor-receptor family member, is a co-stimulatory receptor that can act independently from CD28 to prevent activation-induced death of activated T cells. [Kim Y J, et al. Human 4-1BB regulates CD28 co-stimulation to promote Th1 cell responses. Eur J Immunol 28:881-890 (1998); Hurtado J C, et al. Signals through 4-1BB are costimulatory to previously activated splenic T cells and inhibit activation-induced cell death. J Immunol 158:2600-2609 (1997); DeBenedette M A, et al. Costimulation of CD28− T lymphocytes by 4-1BB ligand. J Immunol 1997; 158:551-559 (1997); Bukczynski J, et al. Costimulation of human CD28− T cells by 4-1BB ligand. Eur J Immunol 33:446-454 (2003)] In our study, we found that chimeric receptors containing 4-1BB can elicit vigorous signals in the absence of CD28− mediated co-stimulation. Cytotoxicity against CD19$^+$ cells mediated by these receptors was as good as that mediated by CD28-containing receptors and was clearly superior to that induced by receptors lacking co-stimulatory molecules. It is known that, in contrast to CD28, 4-1BB stimulation results in a much larger proliferation of CD8$^+$ cells than CD4+ cells. [Shuford W W, et al. 4-1BB costimulatory signals preferentially induce CD8$^+$ T cell proliferation and lead to the amplification in vivo of cytotoxic T cell responses. J Exp Med 1997; 186:47-55 (1997)] We found that T cells expressing the anti-CD19-BB-ζ receptor produced more IL-2 upon stimulation, and that CD8$^+$ cells expanded in the presence of low-dose IL-2 more vigorously than those expressing receptors lacking 4-1BB domains, including those containing CD28. Therefore, the presence of 4-1BB in the chimeric receptors may support more durable T cell responses than those induced by other receptors.

Experimental evidence indicates that harnessing 4-1BB signaling could have useful application in antitumor therapy. Melero et al. Nat Med 3:682-685 (1997) found that antibodies to 4-1BB significantly improved long-lasting remission and survival rates in mice inoculated with the immunogenic P815 mastocytoma cell line. Moreover, immunogenic murine tumor cells made to express 4-1BB ligand were readily rejected and induced long term immunity. [Melero I, et al. Chen L. Amplification of tumor immunity by gene transfer of the co-stimulatory 4-1BB ligand: synergy with the CD28 co-stimulatory pathway. Eur J Immunol 28:1116-1121 (1998)] Dramatic results were also observed in vaccination experiments using other tumor cell lines expressing 4-1BB ligands. [Ye Z, et al. Gene therapy for cancer using single-chain Fv fragments specific for 4-1BB. Nat Med 8:343-348 (2002); Mogi S, et al. Tumour rejection by gene transfer of 4-1BB ligand into a CD80(+) murine squamous cell carcinoma and the requirements of co-stimulatory molecules on tumour and host cells. Immunology 101:541-547 (2000); Yoshida H, et al. A novel adenovirus expressing human 4-1BB ligand enhances antitumor immunity. Cancer Immunol Immunother 52:97-106 (2003)] Of note, experiments with the poorly immunogenic Ag104A fibrosarcoma cell line provided some evidence that 4-1BB could be superior to CD28 in eliciting anti-tumor responses: 80% of mice showed tumor regression with 4-1BB stimulation and 50% of mice with widespread metastasis were cured, [Melero I, Shuford W W, Newby S A, et al. Monoclonal antibodies against the 4-1BB T-cell activation molecule eradicate established tumors. Nat Med 3:682-685 (1997)] whereas CD28 costimulation was not effective alone and required simultaneous CD2 stimulation. [Li Y, et al. Costimulation by CD48 and B7-1 induces immunity against poorly immunogenic tumors. J Exp Med 1996; 183:639-644 (1996)] These data, together with our results, indicate that the addition of 4-1BB to the chimeric receptor should significantly increase the probability that transduced T-cells will survive and continue to proliferate when the receptor is engaged in vivo. We think it noteworthy that T cells with chimeric receptors containing 4-1BB expressed the highest levels of TRAIL upon stimulation, given the known tumoricidal activity of this molecule. [Schmaltz C, et al. T cells require TRAIL for optimal graft-versus-tumor activity. Nat Med 8:1433-1437 (2002)]

Clinical precedents, such as administration of T-cell clones that target CMV epitopes [Walter E A, et al. Reconstitution of cellular immunity against cytomegalovirus in recipients of allogeneic bone marrow by transfer of T-cell clones from the donor. N Engl J Med. 333:1038-1044 (1995)] or EBV-specific antigens, [Rooney C M, et al. Use of gene-modified virus-specific T lymphocytes to control Epstein-Barr-virus-related lymphoproliferation. Lancet 345:9-13 (1995)] attest to the clinical feasibility of adoptive T-cell therapy. Transfer of chimeric receptor-modified T cells has the added advantage of permitting immediate generation of tumor-specific T-cell immunity. Subsequently, therapeutic quantities of antigen-specific T cells can be generated quite rapidly by exposure to target cells and/or artificial antigen-presenting cells, in the presence of ligands of co-stimulatory molecules and/or exogenous cytokines such as IL-2, IL-7, and IL-15. [Geiger T L, Jyothi M D. Development and application of receptor-modified T lymphocytes for adoptive immunotherapy. Transfus Med Rev 15:21-34 (2001); Schumacher T N. T-cell-receptor gene therapy. Nat Rev Immunol. 2:512-519 (2002); Sadelain M, et al. Targeting tumours with genetically enhanced T lymphocytes. Nat Rev Cancer 3:35-45 (2003); Brentjens R J, et al. Eradication of systemic B-cell tumors by genetically targeted human T lymphocytes co-stimulated by CD80 and interleukin-15. Nat Med 9:279-286 (2003)] A specific risk of the strategy proposed here relates to the transforming potential of the retrovirus used to transduce chimeric receptors. [Baum C, Dullmann J, Li Z, et al. Side effects of retroviral gene transfer into hematopoietic stem cells. Blood 101:2099-2114 (2003)] We therefore envisage the coexpression of suicide genes as a safety measure for clinical studies. [Marktel S, et al. Immunologic potential of donor lymphocytes expressing a suicide gene for early immune reconstitution after hematopoietic T-cell-depleted stem cell transplantation. Blood 101:1290-1298 (2003)] This approach would also ensure that the elimination of normal CD19$^+$ B-lineage cells is temporary and should therefore have limited clinical consequences.

In view of the limited effectiveness and the high risk of the currently available treatment options for chemotherapy-refractory B-lineage ALL and other B cell malignancies, the results of our study provide compelling justification for clinical trials using T cells expressing anti-CD19-BB-ζ receptors. Donor-derived T cells endowed with chimeric receptors could replace infusion of non-specific lymphocytes post-transplant. To reduce the risk of GvHD mediated by endogenous T-cell receptors, it may be beneficial to use T cells with restricted endogenous specificity, for example, Epstein-Barrvirus-specific cytotoxic T-lymphocyte lines. [Rossig C, et al. Epstein-Barr virus-specific human T lymphocytes expressing antitumor chimeric T-cell receptors: potential for improved immunotherapy. Blood. 99:2009-2016 (2002)] Therefore, it would be important to test the effects of adding 4-1BB to chimeric receptors transduced in these lines. The reinfusion of autologous T cells collected during clinical remission could also be considered in patients with persistent minimal residual disease. In our experiments, T cells expressing anti-CD19-BB-ζ receptors completely eliminated ALL cells at E:T ratios higher than 1:1, and autologous B lymphocytes became undetectable shortly after transduction of anti-CD19-BB-ζ, suggesting that the potential leukemic cell contamination in the infused products should be greatly reduced or abrogated by the procedure.

9.2 Example 2

T lymphocytes transduced with anti-CD19 chimeric receptors have remarkable anti-ALL capacity in vitro and in vivo, suggesting the clinical testing of receptor-modified autologous T cells in patients with persistent minimal residual disease. However, the use of allogeneic receptor-modified T lymphocytes after hematopoietic cell transplantation (HCT) might carry the risk of severe graft-versus-host disease (GvHD). In this setting, the use of CD3-negative natural killer (NK) cells is attractive because they should not cause GvHD.

Spontaneous cytotoxicity of NK cells against ALL is weak, if measurable at all. To test whether anti-CD19 chimeric receptors could enhance it, we developed methods to specifically expand human primary NK cells and induce high levels of receptor expression. Specific NK cell expansion has been problematic to achieve with established methods which favor CD3+ T cell expansion. Even after T-cell depletion, residual T cells typically become prominent after stimulation.

We overcame this obstacle by generating a genetically-modified K562 myeloid leukemia cell line that expresses membrane-bound interleukin-15 (IL-15) and 4-1BB ligand (CD137L) (K562-mb15-137L). The K562-mb15-137 cell line was generated by retrovirally transducing K562 cells with a chimeric protein construct consisting of human IL-15 mature peptide fused to the signal peptide and transmembrane domain of human CD8 alpha, as well as GFP. Transduced cells were single cell-cloned by limiting dilution and a clone with the highest expression of GFP and membrane-bound (surface) IL-15 was selected. Then, the clone was transduced with human CD137L.

Peripheral blood mononuclear cells from 8 donors were cultured with K562-mb15-137L in the presence of 10 IU/mL IL-2. After 1 week of culture with K562-mb15-137L, NK cells expanded by 16.3±5.9 fold, whereas T cells did not expand. The stimulatory effect of K562-mb15-137L was much higher than that of K562 cells transduced with control vectors, K562 expressing membrane-bound IL-15 or CD137L alone, or K562 expressing wild-type IL-15 instead of membrane-bound IL-15.

NK cells expanded with K562-mb15-137L were transduced with a retroviral vector and the anti-CD19-BB-ζ chimeric receptor. In 27 experiments, mean transduction efficiency (±SD) after 7-14 days was 67.5%±16.7%. Seven to fourteen days after transduction, 92.3% (range 84.7%-99.4%) of cells were CD3-CD56+ NK cells; expression of receptors on the cell surface was high. NK cells expressing anti-CD19-BB-ζ had powerful cytotoxicity against NK-resistant B-lineage ALL cells. NK cells transduced with anti-CD19-BB-ζ had consistently higher cytotoxicity than those transduced with receptors lacking 4-1BB.

Transduction of NK Cells with Chimeric Receptors

Peripheral blood mononuclear cells were stimulated with the K562-mb15-137L cells prior to their exposure to retroviral vectors containing anti-CD19 receptor constructs and GFP. In 10 experiments, median percent of NK cells was 98.4% (93.7-99.4%) 7-11 days after transduction; 77.4% (55.2-90.0%) of these cells were GFP+. We observed high levels of surface expression of the anti-CD19 chimeric receptors.

NK activity against the CD19-negative cells K562 and U937 was not affected by the expression of anti-CD19 receptors. The receptors, however, markedly increased NK activity against CD19+ ALL cells. The following summarizes results obtained with NK cells from 2 donors. At an E:T ratio of 1:1, NK cells from donor 1 lacked cytotoxicity against CD19+ RS4;11 cells and exerted ~50% cytotoxicity against CD19+697 cells after 24 hours. NK cells from donor 2 had no cytotoxicity against RS4;11 or 697 cells. Expression of the anti-CD19-CD3ε receptor overcame NK resistance. NK cells from donor 1 became cytotoxic to RS4;11 cells and those from donor 2 become cytotoxic to both RS;11 and 697 cells. Moreover, when control cells had some cytotoxicity, this was significantly augmented by expression of signaling anti-CD19 receptor.

Subsequently, we found that addition of the co-stimulatory CD28 or 4-1BB to the anti-CD19 receptor markedly enhanced NK cytotoxicity against NK-resistant ALL cells (FIG. 2). For example, after 24 hours of culture at 1:1 E:T ratio, the cytotoxicity mediated by the anti-CD19-BB-ζ receptor against the NK-resistant CD19+ ALL cell lines 380, 697, KOPN57bi and OP1 ranged from 86.5% to 99.1%. Therefore, the inclusion of co-stimulatory molecules enhances not only the cytotoxicity of T lymphocytes but also that of NK cells.

9.3 Example 3

Artificial Antigen Producing Cells (APCs) Pave the Way for Clinical Application by Potent Primary in Vitro Induction Materials and Methods
Cells The CD19 human B-lineage ALL cell lines RS4;11, OP-1, 380, 697, and KOPN57bi; the T-cell line GEM-C7; and the myeloid cell lines K562 and U-937 were available in our laboratory. Cells were maintained in RPMI-1640 (Gibco, Grand Island, N.Y.) supplemented with 10% fetal calf serum (FCS; BioWhittaker, Walkersville, Md.) and antibiotics.

Primary leukemia cells were obtained with appropriate informed consent and Institutional Review Board (M) approval from nine patients with B-lineage ALL; from four of these patients, we also studied (with IRB approval) cryopreserved peripheral blood samples obtained during clinical remission. An unequivocal diagnosis of B-lineage ALL was established by morphologic, cytochemical, and immunophenotypic criteria; in each case, more than 95% of the cells were positive for CD19. Peripheral blood was obtained from eight healthy adult donors. Mononuclear cells collected from the samples by centrifugation on a Lymphoprep density step (Nycomed, Oslo, Norway) were washed twice in phosphate-buffered saline (PBS) and once in AIM-V medium (Gibco).

Plasmids and Retrovirus Production

The anti-CD19-ζ, anti-CD19-BB-i and anti-CD19-truncated (control) plasmids are described in Imai, C, et al., Leukemia 18:676-684 (2004). The pMSCV-IRES-GFP, pEQ-PAM3(-E), and pRDF constructs were obtained from the St.

Jude Vector Development and Production Shared Resource. The intracellular domains of human DAP 10, 4-1BB ligand and interleukin-15 (IL-15) with long signal peptide were subcloned by polymerase chain reaction (PCR) with a human spleen cDNA library (from Dr. G. Neale, St. Jude Children's Research Hospital) used as a template. An antiCD19-DAP 10 plasmid was constructed by replacing the intracellular domain of anti-CD19-ζ with that of DAP 10, using the SOE-PCR (splicing by overlapping extension by PCR) method. The signal peptide of CD8 cc, the mature peptide of IL-15 and the transmembrane domain of CDBα were assembled by SOE-PCR to encode a "membrane-bound" form of IL-15. The resulting expression cassettes were subcloned into EcoRI and XhoI sites of MSCV-IRES-GFP.

The RD114-pseudotyped retrovirus was generated as described in Imai, C, et al., Leukemia 18:676-684 (2004). We used calcium phosphate DNA precipitation to transfect 293T cells with anti-CD19-ζ, anti-CD19-DAP10, anti-CD19-BB-ζ, or anti-CD19-truncated; pEQ-PAM3(-E); and pRDF. Conditioned medium containing retrovirus was harvested at 48 hours and 72 hours after transfection, immediately frozen in dry ice, and stored at −80° C. until use.

Development of K562 Derivatives, Expansion of NK Cells and Gene Transduction

K562 cells were transduced with the construct encoding the "membrane-bound" form of IL-15. Cells were cloned by limiting dilution, and a single-cell clone with high expression of GFP and of surface IL-15 ("K562-mb15") was expanded. This clone was subsequently transduced with human 4-1BB ligand and designated as "K562-mb15-41BBL". K562 cells expressing wild-type IL-15 ("K562-wt15") or 4-IBBL ("K562-41BBL") were produced by a similar procedure. Peripheral blood mononuclear cells (1.5×106) were incubated in a 24-well tissue culture plate with or without 106 K562-derivative stimulator cells in the presence of 10 N/mL human IL-2 (National Cancer Institute BRB Preclinical Repository, Rockville, Md.) in RPMI-1640 and 10% FCS.

Mononuclear cells stimulated with K562-mb15-41BBL were transduced with retroviruses, as previously described for T cells [Melero I, et al., NK1.1 cells express 4-iBB (CDw137) costimulatory molecule and are required for tumor immunity elicited by anti-4-1BB monoclonal antibodies. Cell Immunol 190:167-172 (1998)]. Briefly, 14-mL polypropylene centrifuge tubes (Falcon) were coated with human fibronectin (100 μg/mL; Sigma, St. Louis, Mo.) or RetroNectin (50 μg/mL; TaKaRa, Otsu, Japan). Prestimulated cells (2×10$^5$) were resuspended in the tubes in 2-3 mL of virus-conditioned medium with polybrene (4 μg/mL; Sigma) and centrifuged at 2400×g for 2 hours (centrifugation was omitted when RetroNectin was used). The multiplicity of infection (4 to 6) was identical in each experiment comparing the activity of different chimeric receptors. After centrifugation, cells were left undisturbed for 24 hours in a humidified incubator at 37° C., 5% CO$_2$. The transduction procedure was repeated on two successive days. After a second transduction, the cells were re-stimulated with K562-mb 15-4 1BBL in the presence of 10 IU/mL of IL-2. Cells were maintained in RPMI-1640, 10% FCS, and 10 IU/mL IL-2.

Detection of Chimeric Receptor Expression and Immunophenotyping

Transduced NK cells were stained with goat anti-mouse (Fab)$^2$ polyclonal antibody conjugated with biotin (Jackson Immunoresearch, West Grove, Pa.) followed by streptavidin conjugated to peridinin chlorophyll protein (PerCP; Becton Dickinson, San Jose, Calif.). For Western blotting, cells were lysed in RIPA buffer (PBS, 1% Triton-X100, 0.5% sodium deoxycholate, 0.1% SDS) containing 3 μg/mL of pepstatin, 3 μg/mL of leupeptin, 1 mM of PMSF, 2 mM of EDTA, and 5 μg/mL of aprotinin. Centrifuged lysate supernatants were boiled with an equal volume of loading buffer with or without 0.1 M DTT, and then separated by SDS PAGE on a precast 10-20% gradient acrylamide gel (BioRad, Hercules, Calif.). The proteins were transferred to a PVDF membrane, which was incubated with primary mouse anti-human CD3ζ monoclonal antibody (clone 8D3; Pharmingen). Membranes were then washed, incubated with a goat anti-mouse IgG horseradish peroxidase-conjugated second antibody, and developed by using the ECP kit (Pharmacia, Piscataway, N.J.).

The following antibodies were used for immunophenotypic characterization of expanded and transduced cells: anti-CD3 conjugated to fluorescein isothiocyanate (FITC), to peridinin chlorophyll protein (PerCP) or to energy-coupled dye (ECD); anti-CD10 conjugated to phycoerythrin (PE); anti-CD19 PE; anti-CD22 PE; anti-CD56 FITC, PE or allophycocyanin (AFC); anti-CD16 CyChrome (antibodies from Becton Dickinson; Pharmingen, San Diego; or Beckman-Coulter, Miami, Fla.); and anti-CD25 PE (Dako, Carpinteria, Calif.). Surface expression of KIR and NK activation molecules was determined with specific antibodies conjugated to FIX or PE (from Beckman-Coulter or Becton-Dickinson), as previously described [Brentjens R J, Latouche J B, Santos E, et al. Eradication of systemic B-cell tumors by genetically targeted human T lymphocytes co-stimulated by CD80 and interleukin-15. Nat Med 9:279-286 (2003)]. Antibody staining was detected with a FACScan or a LSR II flow cytomete (Becton Dickinson).

Cytotoxicity Assays and Cytokine Production

Target cells (1.5×105) were placed in 96-well U-bottomed tissue culture plates (Costar, Cambridge, Mass.) and incubated with primary NK cells transduced with chimeric receptors at various effector:target (E:T) ratios in RPMI-1640 supplemented with 10% FCS; NK cells were cultured with 1000 U/mL IL-2 for 48 hours before the assay. Cultures were performed in the absence of exogenous IL-2. After 4 hours and 24 hours, cells were harvested, labeled with CD10 PE or CD22 PE and CD56 FITC, and assayed by flow cytometry as previously described. The numbers of target cells recovered from cultures without NK cells were used as a reference.

For cytokine production, primary NK cells (2×10$^5$ in 200 μl) expressing chimeric receptors were stimulated with various target cells at a 1:1 ratio for 24 hours. The levels of IFN-γ and GM-CSF in cell-free culture supernatants were determined with a Bio-Plex assay (BioRad).

Statistical Analysis

A test of equality of mean NK expansion with various stimuli was performed using analysis of variance for a randomized complete block design with each donor considered a random block. Tukey's honest significant difference procedure was used to compute simultaneous confidence intervals for each pairwise comparison of the differences of treatment means. Differences in cytotoxicities and cytokine production among NK cells bearing different chimeric receptors were analyzed by the paired Student's t test.

Results

Culture Conditions that Favor the Expansion of Primary NK Cells

To transduce chimeric receptors into primary NK cells, we searched for stimuli that would induce specific NK cell proliferation. In preliminary experiments, peripheral blood mononuclear cells of CD3$^+$ T lymphocytes were depleted and the remaining cells were stimulated with IL-2 (1000 U/mL) or IL-15 (10 ng/mL). Under these culture conditions there was no expansion of NK cells, which in fact progressively declined in numbers. With PHA (7 mg/mL) and IL-2 (1000

U/mL) as stimuli, we observed a 2- to 5-fold expansion of CD56+ CD3− NK cells after 1 week of culture. However, despite the low proportion of contaminating CD3+ cells (<2% in two experiments) at the beginning of the cultures, these cells expanded more than NK cells (>30-fold expansion), and after 1 week of culture represented approximately 35% of the cell population.

NK cells can be stimulated by contact with the human leukemia cell line K562, which lacks HLA-antigen expression, [Robertson M J, Cameron C, Lazo S, Cochran K J, Voss S D, Ritz J. Costimulation of human natural killer cell proliferation: role of accessory cytokines and cell contact-dependent signals. Nat Immun 15:213-226 (1996)] and genetically modified K562 cells have been used to stimulate cytotoxic T lymphocytes [Maus M V, Thomas A K, Leonard D G, et al. Ex vivo expansion of polyclonal and antigen-specific cytotoxic T lymphocytes by artificial APCs expressing ligands for the T-cell receptor, CD28 and 4-1BB. Nat Biotechnol 20:143-148 (2002)]. We tested whether the NK-stimulatory capacity of K562 cells could be increased through enforced expression of additional NK-stimulatory molecules, using two molecules that are not expressed by K562 cells and are known to stimulate NK cells. One molecule, the ligand for 4-1BB (4-1BBL), triggers activation signals after binding to 4-1BB (CD137), a signaling molecule expressed on the surface of NK cells [Melero I, Johnston J V, Shufford W W, Mittler R S, Chen L. NK1.I cells express 4-IBB (CDw137) costimulatory molecule and are required for tumor immunity elicited by anti-4-IBB monoclonal antibodies. Cell Immunol 190:167-172 (1998)]. The other molecule, IL-15, is a cytokine known to promote NK-cell development and the survival of mature NK cells [Carson W E, Fehniger T A, Haldar S, et al. A potential role for interleukin-15 in the regulation of human natural killer cell survival J Clin Invest. 99:937-943 (1997); Cooper M A, Bush J E, Fehniger T A, et al. In vivo evidence for a dependence on interleukin 15 for survival of natural killer cells. Blood 100:3633-3638 (2002); Fehniger T A, Caligiuri M A. Ontogeny and expansion of human natural killer cells: clinical implications. Int Rev Immunol 20:503-534 (2001); Wu J, Lanier L L. Natural killer cells and cancer. Adv Cancer Res 90:127-56.:127-156 (2003)]. Since IL-15 has greater biological activity when presented to NK cells bound to IL-15Rα on the cell membrane of stimulatory cells, rather than in its soluble form, we made a construct containing the human IL-15 gene fused to the gene encoding the human CD8α, transmembrane domain, and used it to transduce K562 cells. Expression of IL-15 on the surface of K562 cells was more than five times higher with the IL-15-CD8α construct than with wild-type IL-15.

To test whether the modified K562 cells expressing both 4-11313L and IL-I5 (K562mb15-41BBL cells) promote NK cell expansion, we cultured peripheral blood mononuclear cells from seven donors in the presence of low-dose (10 U/mL) IL-2 as well as irradiated K562 cells transduced with 4-1BBL and/or IL-15, or with an empty control vector. Expression of either 4-1BBL or IL-15 by K562 cells improved the stimulation of NK-stimulatory capacity of K562 in some cases but not overall, whereas simultaneous expression of both molecules led to a consistent and striking amplification of NK cells (median recovery of CD56+ CD3− cells at 1 week of culture, 2030% of input cells [range, 1020%-2520%] compared with a median recovery of 250% [range, 150%-640%] for K562 cells lacking 4-1BBL and IL-15; P<0.0001). In 24 experiments with cells from 8 donors, NK-cell expansion after 3 weeks of culture with K562 cells expressing both stimulatory molecules ranged from 309-fold to 12,409 fold (median, 1089-fold). Neither the modified nor unmodified K562 cells caused an expansion of T lymphocytes. Among expanded CD56+ CD3− NK cells, expression of CD56 was higher than that of unstimulated cells; expression of CD16 was similar to that seen on unstimulated NK cells (median CD16+ NK cells in 7 donors: 89% before expansion and 84% after expansion). We also compared the expression of KIR molecules on the expanded NK cells with that on NK cells before culture, using the monoclonal antibodies CD158a (against KIR 2DL1), CD158b (2DL2), NKBI (3DL1) and NKAT2 (2DL3). The prevalence of NK subsets expressing these molecules after expansion resembled that of their counterparts before culture, although the level of expression of KIR molecules was higher after culture. Similar results were obtained for the inhibitory receptor CD94, while expression of the activating receptors NKp30 and NKp44 became detectable on most cells after culture. In sum, the immunophenotype of expanded NK cells reiterated that of activated NK cells, indicating that contact with K562-mb1541BBL cells had stimulated expansion of all subsets of NK cells.

Transduction of NK Cells with Chimeric Receptors

Before transducing peripheral blood mononuclear cells with retroviral vectors containing chimeric receptor constructs and GFP, we stimulated them with K562-mb15-41BBL cells. In 27 experiments, the median percentage of NK cells that were GFP+ at 7-11 days after transduction was 69% (43%-93%). Chimeric receptors were expressed at high levels on the surface of NK cells and, by Western blotting, were in both monomeric and dimeric configurations.

To identify the specific signals required to stimulate NK cells with chimeric receptors, and overcome inhibitory signals mediated by KIR molecules and other NK inhibitory receptors that bind to HLA class I molecules, we first compared two types of chimeric receptors containing different signaling domains: CD3ζ, a signal-transducing molecule containing three immunoreceptor tyrosine-based activation motifs (ITAMs) and linked to several activating receptors expressed on the surface of NK cells [Farag S S, Fehniger T A, Ruggeri L, Velardi A, Caligiuri M A. Natural killer cell receptors: new biology and insights into the graft-versus-leukemia effect. Blood 100:1935-1947 (2002); Moretta L, Moretta A. Unravelling natural killer cell function: triggering and inhibitory human NK receptors. EMBO J 23:255-259 (2004)], and DAP 10, a signal transducing molecule with no ITAMs linked to the activating receptor NKG2D and previously shown to trigger NK cytotoxicity [Farag S S, Fehniger T A, Ruggeri L, Velardi A, Caligiuri M A. Natural killer cell receptors: new biology and insights into the graft-versus-leukemia effect. Blood 100:1935-1947 (2002); Moretta L, Moretta A. Unravelling natural killer cell function: triggering and inhibitory human NK receptors. EMBO J 23:255-259 (2004); Billadeau D D, Upshaw J L, Schoon R A, Dick C J, Leibson P J. NKG2D-DAPIO triggers human NK cell-mediated killing via a Syk-independent regulatory pathway. Nat ImmuNo. 4:557-564 (2003)]. As a control, we used NK cells transduced with a vector containing an antiCD19 receptor but no signaling molecules or containing GFP alone.

NK cells were challenged with the CD19+ leukemic cell lines 380, 697 and RS4;11, all of which express high levels of HLA-class I molecules by antibody staining By genotyping, RS4;11 is Cw4/Cw3, Bw4 and A3; 380 is Cw4/Cw4, Bw4; and 697 is Cw3/Cw3. Hence, these cell lines were fully capable of inhibiting NK cell cytotoxicity via binding to NK inhibitory receptors.

Expression of receptors without signaling molecules did not increase NK-mediated cytotoxicity over that exerted by NK cells transduced with the vector containing only GFP. By contrast, expression of anti-CD19-ζ receptors markedly enhanced NK cytotoxicity in all experiments, regardless of the intrinsic ability of donor NK cells to kill leukemic targets. For example, 380 cells were highly resistant to NK cells from donors 2 and 3, but were killed when these donor cells expressed anti-CD19-ζ receptors. Similar observations were made for RS4;11 cells and the NK cells of donor 1 and for 697 cells and NK cells of donor 2. Moreover, the anti-CD19-ζ receptors led to improved killing of target cells even when natural cytotoxicity was present. In all experiments, the cytotoxicity triggered by the anti-CD19-ζ receptor was enhanced over that achieved by replacing CD3ζ with DAP 10 ($P<0.001$).

4-1BB-Mediated Costimulatory Signals Enhance NK Cytotoxicity

Previous studies have shown that the addition of costimulatory molecules to chimeric receptors enhances the proliferation and cytotoxicity of T lymphocytes [Imai C, Mihara K, Andreansky M, Nicholson I C, Pui C H, Campana D. Chimeric receptors with 4-1BB signaling capacity provoke potent cytotoxicity against acute lymphoblastic leukemia. Leukemia 18:676-684 (2004)]. Of the two best known costimulatory molecules in T lymphocytes, CD28 and 4-1BB, only 4-1BB is expressed by NK cells [Melero I, Johnston J V, Shufford W W, Mittler R S, Chen L. NKLI cells express 4-1BB (CDw137) costimulatory molecule and are required for tumor immunity elicited by anti-4-1BB monoclonal antibodies. Cell Immunol 1998; 190:167-172 (1998); Lang S, Vujanovic N L, Wollenberg B, Whiteside T L. Absence of B7.1-CD28/CTLA-4 mediated co-stimulation in human NK cells. Eur J Immunol 28:780-786 (1998); Goodier M R, Londei M. CD28 is not directly involved in the response of human CD3CD56+ natural killer cells to lipopolysaccharide: a role for T cells. Immunology 111:384-390(2004)]. We determined whether the addition of 4-1BB to the anti-CD19-ζ receptor would enhance NK cytotoxicity. In a 4 hour-cytotoxicity assay, cells expressing the 41BB-augmented receptor showed a markedly better ability to kill CD19+ cells than did cells lacking this modification. The superiority of NK cells bearing the anti-CD19-BB-ζ receptor was also evident in 24-hour assays with NK cells from different donors cultured at a 1:1 ratio with the leukemia cell lines 697, KOPN57bi and OP-1.

Next, we determined whether the antileukemic activity of NK cells expressing anti-CD19-BB-ζ receptors extended to primary leukemic samples. In five samples from children with different molecular species of ALL, NK cells expressing the 4-1BB receptors exerted strong cytotoxicity that was evident even at low E:T ratios (e.g., <1:1; FIG. 7) and uniformly exceeded the activity of NK cells expressing signaling receptors that lacked 4-1BB. Even when donor NK cells had natural cytotoxicity against ALL cells and CD3ζ receptor did not improve it, addition of 4-1BB to the receptor significantly enhanced cytotoxicity. Consistent with their increased cytotoxicity, NK cells expressing anti-CD19-BB-ζ mediated more vigorous activation signals. Forty-six percent of NK cells bearing this receptor expressed the IL2 receptor a chain CD25 after 24 hours of coculture with CD19+ ALL cells, compared with only 17% of cells expressing the anti-CD19-ζ receptor and <1% for cells expressing receptors that lacked stimulatory capacity. Moreover, anti-CD19-BB-C receptors induced a much higher production of IFN-g and GM-CSF upon contact with CD19+ cells than did receptors without 41BB.

We asked whether the expression of signaling chimeric receptors would affect spontaneous NK activity against NK-sensitive cell lines not expressing CD19. Spontaneous cytotoxicity of NK cells from three donors against the CD19− leukemia cell lines K562, U937 and CEM-C7 was not diminished by expression of chimeric receptors, with or without 4-1BB.

Anti-CD19 Chimeric Receptors Induce NK Cytotoxicity Against Autologous Leukemic Cells To determine whether the NK cell expansion and transduction system that we developed would be applicable to clinical samples, we studied peripheral blood samples that had been obtained (and cryopreserved) from four patients with childhood B-lineage ALL in clinical remission, 25-56 weeks from diagnosis. NK cell expansion occur in all four samples: recovery of after one week of culture with K562-mb15-41BBL cells, recovery of CD56+ CD3− NK cells ranged from 1350% to 3680% of the input.

After transduction with chimeric receptors, we tested the cytotoxicity of the NK cells against autologous leukemic lymphoblasts obtained at diagnosis. Expression of anti-CD19-BB-ζ receptors overcame NK cell resistance of autologous cells; NK cells expressing the receptors exerted cytotoxicity which was as powerful as that observed with allogeneic targets.

Discussion

In this study, we demonstrated that the resistance of cancer cells to NK cell activity can be overcome by chimeric receptors expressed on primary NK cells. The stimulatory signals triggered by the receptors upon contact with target cells predominated over inhibitory signals and induced powerful cytotoxicity against NK-resistant leukemic cell lines and primary leukemic cells. We found that the type of stimulatory signal delivered by the chimeric receptor was a key factor in inducing cytotoxicity. Although DAP 10 signaling can elicit NK cytotoxicity, chimeric receptors containing this molecule in our study induced weaker NK cell activity than that generated by CD3ζ-containing receptors, despite identical levels of surface expression. We also found that addition of the costimulatory molecule 4-1BB to the chimeric receptors markedly augmented cytotoxicity, and that receptors containing both CD3ζ and 4-1BB triggered a much more robust NK cell activation and cytokine production than did those containing only CD3ζ.

The important contribution of 4-1BB signals agrees with findings that anti-4-1BB antibodies activate murine NK cells [Pan P Y, et al., Regulation of dendritic cell function by NK cells: mechanisms underlying the synergism in the combination therapy of IL-12 and 4-1BB activation. J Immunol 172: 4779-4789 (2004)], and enhance their anti-tumor activity. Leukemic lymphoid cells usually do not express 4-1BB ligand: only 2 of 284 diagnostic B-lineage ALL samples studied by gene arrays at our institution expressed 4-1BB ligand transcripts [Yeoh E J, et al., Classification, subtype discovery, and prediction of outcome in pediatric acute lymphoblastic leukemia by gene expression profiling. Cancer Cell 1:133-143 (2002)]. Hence, 4-1BB signals can be delivered to NK cells only if the molecule is incorporated into the receptor.

Efficient and stable transduction of primary NK cells is notoriously difficult, prompting us to devise a new gene transduction method for the present study. Most investigators have demonstrated efficient gene transfer only in continuously growing NK cell lines [Roberts M R, et al., Antigen-specific cytolysis by neutrophils and NK cells expressing chimeric immune receptors bearing zeta or gamma signaling domains. J Immunol. 161:375-384 (1998); Nagashima S, et al., Stable transduction of the interleukin-2 gene into human natural killer cell lines and their phenotypic and functional characterization in vitro and in vivo. Blood 91:3850-3861(1998)] or reported methods yielding only transient gene expression [Billadeau D D, et al., NKG2D-DAP 10 triggers human NK cell-mediated killing via a Syk-independent regulatory pathway. Nat ImmuNo. 4:557-564 (2003); Trompeter H I, et al., Rapid and highly efficient gene transfer into natural killer cells by nucleofection. J Immunol Methods 274:245-256 (2003); Schroers R, et al., Gene transfer into human T lymphocytes and natural killer cells by Ad5/F35 chimeric adenoviral vectors. Exp Hematol 32:536-546(2004)]. We achieved stable expression of chimeric receptors in primary CD56$^+$ CD3$^-$ NK cells by using an RD114-pseudotyped retroviral vector and specifically expanding primary CD56$^+$ CD3$^-$ NK cells before they were exposed to the retrovirus, a step that allowed highly efficient gene expression. Although several cytokines such as IL-2, IL-12 and IL-15 have been reported to stimulate NK cells [Carson W E, et al., A potential role for interleukin-15 in the regulation of human natural killer cell survival J Clin Invest. 99:937-943 (1997); Trinchieri G, et al., Response of resting human peripheral blood natural killer cells to interleukin 2 J Exp Med 1984; 160: 1147-1169 (1984); Naume B, et al., A comparative study of IL-12 (cytotoxic lymphocyte maturation factor)-, IL-2-, and IL-7-induced effects on immunomagnetically purified CD56+ NK cells. J Immunol 148:2429-2436 (1992)], their capacity to induce proliferation of resting CD56$^+$ CD3 cells has been poor, unless accessory cells are present in the cultures. Perussia et al. Nat Immun Cell Growth Regul 6:171-188 (1987), found that contact with irradiated B-lymphoblastoid cells induced as high as a 25-fold expansion of NK cells after 2 weeks of stimulation, while Miller et al. Blood; 80:2221-2229 (1992) reported an approximate 30-fold expansion of NK cells after 18 days of culture with 1000 U/mL IL-2 and monocytes. However, these culture conditions are likely to promote the growth of CD3$^+$ T lymphocytes as well as NK cells. Since our ultimate aim is to generate pure preparations for out donor NK cells devoid of CD3$^+$ T lymphocytes, that can be infused into recipients of allogeneic hematopoietic stem cell transplants, we searched for methods that would maximize NK cell expansion without producing T-cell mitogenicity.

Contact with K562 cells (which lack MHC-class I molecule expression and hence do not trigger KIR-mediated inhibitory signals in NK cells) is known to augment NK cell proliferation in response to IL-15. We found that membrane-bound IL-15 and 4-1BBL, coexpressed by K562 cells, acted synergistically to augment K562-specific NK stimulatory capacity, resulting in vigorous expansion of peripheral blood CD56$^+$ CD3$^-$ NK cells without concomitant growth of T lymphocytes. After 2-3 weeks of culture, we observed NK cell expansions of up to 10,000-fold, and virtually pure populations of NK cells could be obtained, even without the need for T-cell depletion in some cases. NK cells expanded in this system retained the immunophenotypic diversity seen among peripheral blood subsets of NK cells, as well as their natural cytotoxicity against sensitive target cells, even after transduction with different chimeric receptors. Hence, this system should help studies of NK cell biology which require specific cell expansion and/or gene transduction, but it should also be adaptable to clinical applications after generating K562mb 15-4 1 BBL cells that comply with current good manufacturing practices for clinical trials. Recently, Harada et al. reported that expansions of CD56$^+$ CD3$^-$ cells (up to 400-fold after 2 weeks) were apparently superior after contact with another HLA class I-negative cell line, the Wilms tumor cell line HFWT [Harada H, Saijo K, Watanabe S, et al. Selective expansion of human natural killer cells from peripheral blood mononuclear cells by the cell line, HFWT. Jpn J Cancer Res 93:313 (2002)]. Future studies should determine whether HFWT cells express 41BBL or whether enforced expression of 4-1BBL together with IL-15 results in a greater specific expansion of NK cells than seen with modified K562 cells.

In the context of allogeneic hematopoietic stem cell transplantation, infusions of activated donor T cells would carry an unacceptably high risk of severe GvHD, particularly in recipients of haploidentical or mismatched transplants. By contrast, infusions of pure CD56 CD3 NK cells should not impose that risk [Ruggeri L, et al., Effectiveness of donor natural killer cell alloreactivity in mismatched hematopoietic transplants. Science 295:2097-2100 (2002)]. Most clinical studies of the therapeutic effects of NK cells have been performed in an autologous setting and have yielded only moderately promising results [Farag S S, et al., Natural killer cell receptors: new biology and insights into the graft-versus-leukemia effect. Blood 100:1935-1947 (2002); Chiorean E G, Miller J S. The biology of natural killer cells and implications for therapy of human disease. J Hematother Stem Cell Res 10:451-463 (2001)]. This is not surprising because NK cell activity is inhibited by surface receptors that recognize autologous HLA molecules expressed by both normal and neoplastic cells. Allogeneic NK cells may be more effective, but even in an allogeneic setting the capacity of NK cells to kill malignant lymphoid cells is generally modest and often negligible [Caligiuri M A, Velardi A, Scheinberg D A, Borrello I M. Immunotherapeutic approaches for hematologic malignancies. Hematology (Am Soc Hematol Educ Program) 337-353 (2004)]. Leung et al. [ J Immunol 172:644-650 (2004)] detected NK cytotoxicity against an ALL cell line expressing particularly low levels of inhibitory HLA molecules, but cytotoxicity was much lower than that observed against the NK-cell target K562: only about 50% of the ALL cells were killed at an effector:target ratio of 40:1. In that study, RS4;11 cells, which express HLA-C alleles that bind the most commonly expressed KIRs, were NK-resistant, whereas these cells, as well as autologous leukemic cells, were highly sensitive to NK cells expressing anti-CD19 signaling receptors in our study. NK cells expressing signaling chimeric receptors have much more powerful antileukemic activity than unmodified NK cells, and can kill target cells irrespective of their HLA profile. An increased understanding of the signals leading to immune cell activation, together with progress in gene cloning and transfer, have made the treatment of cancer with "adoptively acquired immunity" a realistic goal. Clinical precedents, such as administration of T-cell clones that target cytomegalovirus epitopes [Walter E A, et al., Reconstitution of cellular immunity against cytomegalovirus in recipients of allogeneic bone marrow by transfer of T-cell clones from the donor. N Engl J Med 1995; 333: 1038-1044 (1995)] or EBV-specific antigens [Rooney C M, et al., Use of gene-modified virus-specific T lymphocytes to control Epstein-Barr-virus-related lymphoproliferation. Lancet 345:9-13(1995)], attest to the clinical feasibility of adoptive immune cell therapy. Nonetheless, there are potential limitations that may affect the effectiveness of cell therapy guided by chimeric receptors. One is that the murine scFv portion of the chimeric receptor or the fusion sites of the human regions that compose it may trigger a host immune response leading to elimination of the modified cells [Sadelain M, et al., Targeting tumours with genetically enhanced T lymphocytes. Nat Rev Cancer 3:35-45 (2003)]. Although the impact of such an event in a clinical setting remains to be determined, we anticipate that immune responses against modified NK cells will be limited in immune-suppressed patients after hematopoietic stem cell transplantation. Another potential limitation is that adoptively transferred cells may have inadequate persistence in vivo, although a recent study showed that NK cells obtained from haploidentical donors and activated ex vivo could expand in patients when infused after administration of high-dose cyclophosphamide and fludarabine, which caused an increased in endogenous IL-15 [Miller J S, et al., Successful adoptive transfer and in vivo expansion of human haploidentical NK cells in cancer patients. Blood; in press (2005)]. We speculate that such expansions would also occur with genetically-modified NK cells, and suggest that further studies to identify signaling molecules that promote NK cell proliferation when incorporated into chimeric receptors are warranted. In patients at a high risk of leukemia or lymphoma relapse, the expected benefits of genetically-modified NK cells will outweigh the risk of insertional oncogenesis posed by the use of retroviruses for chimeric receptor transduction [Baum C, et al., Side effects of retroviral gene transfer into hematopoietic stem cells. Blood 101:2099-2114 (2003)]. We also predict that the coexpression of suicide genes will become a useful safety measure in clinical studies [Marktel S, et al., Immunologic potential of donor lymphocytes expressing a suicide gene for early immune reconstitution after hematopoietic T-cell-depleted stem cell transplantation. Blood 101:1290-1298 (2003)]; this strategy would also ensure that the elimination of normal CD19+ B-lineage cells is only temporary.

Novel therapies that bypass cellular mechanisms of drug resistance are urgently needed for patients with refractory leukemia and lymphoma. NK cell alloreactivity is a powerful new tool for improving the therapeutic potential of allogeneic hematopoietic stem cell transplantation. The results of this study indicate that signaling receptors can enhance the efficacy of NK cell alloreactivity and widen its applicability. We envisage initial clinical trials in which donor NK cells, collected by apheresis, are expanded ex vivo as described here, transduced with chimeric receptors and then infused after transplantation in patients with B-lineage ALL. The target molecule for the chimeric receptors, CD19, was selected because it is one of the most widely expressed surface antigens among B-cell malignancies, including ALL, CLL and NHL. In these malignancies, CD19 is highly expressed on the surface of virtually all cells but has limited or no expression in normal tissues [Campana D, Behm F G. Immunophenotyping of leukemia. J Immunol Methods 243:59-75 (2000)]. However, the NK-cell strategy of immunotherapy we describe would not have to be directed to the CD19 antigen, but could be applied to any of the numerous molecules identified as potential targets for chimeric receptor-based cell therapy in cancer patients.

All of the above U.S. patents, U.S. patent application publications, U.S. patent applications, foreign patents, foreign patent applications and non-patent publications referred to in this specification, including but not limited to U.S. patent application Ser. No. 09/960,264, filed Sep. 20, 2001; and U.S. application Ser. No. 10/981,352, filed Nov. 4, 2004, are incorporated herein by reference, in their entirety. All of references, patents, patent applications, etc. cited above, are incorporated herein in their entirety.

What is claimed is:

1. A polynucleotide encoding a chimeric receptor comprising: (a) an extracellular ligand-binding domain comprising an anti-CD19 single chain variable fragment (scFv) domain; (b) a transmembrane domain; and (c) a cytoplasmic domain comprising a 4-1BB signaling domain and a CD3ζ signaling domain.

2. A vector comprising a polynucleotide encoding a chimeric receptor comprising: (a) an extracellular ligand-binding domain comprising an anti-CD19 single chain variable fragment (scFv) domain, (b) a transmembrane domain, and (c) a cytoplasmic domain comprising a 4-1BB signaling domain and a CD3ζ signaling domain, wherein the polynucleotide encoding the chimeric receptor is operatively linked to at least one regulatory element for expression of the chimeric receptor.

3. An isolated host cell comprising a polynucleotide encoding a chimeric receptor comprising: (a) an extracellular ligand-binding domain comprising an anti-CD19 single chain variable fragment (scFv) domain; (b) a transmembrane domain; and (c) a cytoplasmic domain comprising a 4-1BB signaling domain and a CD3ζ signaling domain.

4. The isolated host cell of claim 3 which is a T lymphocyte or an NK cell.

5. The isolated host cell of claim 3 which is a T lymphocyte.

6. The polynucleotide of claim 1 wherein the signaling domain is a human 4-1BB signaling domain.

7. The polynucleotide of claim 6, Wherein the 4-1BB signaling domain comprises amino acids 214-255 of SEQ ID NO:2.

8. The polynucleotide of claim 7, wherein the nucleotide sequence encoding the human 4-1BB signaling domain comprises nucleotide residues 129-893 of SEQ ID NO:1.

9. The polynucleotide of claim 1, wherein the transmembrane domain is the transmembrane domain of CD8α.

10. The polynucleotide of claim 9, wherein the extracellular ligand-binding domain further comprises a signal peptide of CD8α.

11. The vector of claim 2 which is a viral vector.

12. The vector of claim 11 which is a retroviral vector.

13. The isolated host cell of claim 3 which is an NK cell.

14. The isolated host cell of claim 3 which is an autologous cell isolated from a patient having a cancer of B cell origin.

15. The isolated host cell of claim 14, wherein the autologous cell is an autologous T lymphocyte.

16. The isolated host cell of claim 15, wherein the autologous T lymphocyte is derived from a blood or tumor sample of a patient having a cancer of B cell origin and activated and expanded in vitro.

17. The isolated host cell of claim 5, wherein the T lymphocyte is an activated T lymphocyte.

18. The isolated host cell of claim 5, wherein the T lymphocyte is isolated from a blood or tumor sample of a patient having a cancer of B cell origin.

19. The isolated host cell of claim 18 wherein the host cell is isolated from a patient having lymphoblastic leukemia, B-lineage acute lymphoblastic leukemia, B-cell chronic lymphocytic leukemia or B-cell non-Hodgkin's lymphoma.

20. The polynucleotide of claim 1, wherein the chimeric receptor further comprises a hinge domain.

21. The vector of claim 2, wherein the chimeric receptor further comprises a hinge domain.

22. The isolated cell of claim 3, wherein the chimeric receptor further comprises a hinge domain.

* * * * *

SEQUENCE LISTING

```
<160> NUMBER OF SEQ ID NOS: 4

<210> SEQ ID NO 1
<211> LENGTH: 1935
<212> TYPE: DNA
<213> ORGANISM: Homo sapiens
<220> FEATURE:
<221> NAME/KEY: CDS
<222> LOCATION: (129)..(893)

<400> SEQUENCE: 1
agaccaagga gtggaaagtt ctccggcagc cctgagatct caagagtgac atttgtgaga      60
ccagctaatt tgattaaaat tctcttggaa tcagctttgc tagtatcata cctgtgccag     120 atttcatc atg gga aac agc tgt tac aac ata gta gcc act ctg ttg ctg     170
         Met Gly Asn Ser Cys Tyr Asn Ile Val Ala Thr Leu Leu Leu
           1               5                  10 gtc ctc aac ttt gag agg aca aga tca ttg cag gat cct tgt agt aac     218
Val Leu Asn Phe Glu Arg Thr Arg Ser Leu Gln Asp Pro Cys Ser Asn
 15                  20                  25                  30 tgc cca gct ggt aca ttc tgt gat aat aac agg aat cag att tgc agt     266
Cys Pro Ala Gly Thr Phe Cys Asp Asn Asn Arg Asn Gln Ile Cys Ser
                 35                  40                  45 ccc tgt cct cca aat agt ttc tcc agc gca ggt gga caa agg acc tgt     314
Pro Cys Pro Pro Asn Ser Phe Ser Ser Ala Gly Gly Gln Arg Thr Cys
             50                  55                  60 gac ata tgc agg cag tgt aaa ggt gtt ttc agg acc agg aag gag tgt     362
Asp Ile Cys Arg Gln Cys Lys Gly Val Phe Arg Thr Arg Lys Glu Cys
         65                  70                  75 tcc tcc acc agc aat gca gag tgt gac tgc act cca ggg ttt cac tgc     410
Ser Ser Thr Ser Asn Ala Glu Cys Asp Cys Thr Pro Gly Phe His Cys
     80                  85                  90
```

```
ctg ggg gca gga tgc agc atg tgt gaa cag gat tgt aaa caa ggt caa    458
Leu Gly Ala Gly Cys Ser Met Cys Glu Gln Asp Cys Lys Gln Gly Gln
 95             100                 105                 110 gaa ctg aca aaa aaa ggt tgt aaa gac tgt tgc ttt ggg aca ttt aac    506
Glu Leu Thr Lys Lys Gly Cys Lys Asp Cys Cys Phe Gly Thr Phe Asn
            115                 120                 125 gat cag aaa cgt ggc atc tgt cga ccc tgg aca aac tgt tct ttg gat    554
Asp Gln Lys Arg Gly Ile Cys Arg Pro Trp Thr Asn Cys Ser Leu Asp
        130                 135                 140 gga aag tct gtg ctt gtg aat ggg acg aag gag agg gac gtg gtc tgt    602
Gly Lys Ser Val Leu Val Asn Gly Thr Lys Glu Arg Asp Val Val Cys
    145                 150                 155 gga cca tct cca gcc gac ctc tct ccg gga gca tcc tct gtg acc ccg    650
Gly Pro Ser Pro Ala Asp Leu Ser Pro Gly Ala Ser Ser Val Thr Pro
160                 165                 170 cct gcc cct gcg aga gag cca gga cac tct ccg cag atc atc tcc ttc    698
Pro Ala Pro Ala Arg Glu Pro Gly His Ser Pro Gln Ile Ile Ser Phe
175                 180                 185                 190 ttt ctt gcg ctg acg tcg act gcg ttg ctc ttc ctg ctg ttc ttc ctc    746
Phe Leu Ala Leu Thr Ser Thr Ala Leu Leu Phe Leu Leu Phe Phe Leu
                195                 200                 205 acg ctc cgt ttc tct gtt gtt aaa cgg ggc aga aag aaa ctc ctg tat    794
Thr Leu Arg Phe Ser Val Val Lys Arg Gly Arg Lys Lys Leu Leu Tyr
                210                 215                 220 ata ttc aaa caa cca ttt atg aga cca gta caa act act caa gag gaa    842
Ile Phe Lys Gln Pro Phe Met Arg Pro Val Gln Thr Thr Gln Glu Glu
            225                 230                 235 gat ggc tgt agc tgc cga ttt cca gaa gaa gaa gaa gga gga tgt gaa    890
Asp Gly Cys Ser Cys Arg Phe Pro Glu Glu Glu Glu Gly Gly Cys Glu
        240                 245                 250 ctg                                                                 943
Leu
255 aaatatgagt catccgctat cacagctttc aaaagcaaga acaccatcct acataatacc   1003 caggattccc ccaacacacg ttcttttcta aatgccaatg agttggcctt taaaaatgca   1063 ccacttttt tttttttttg acagggtctc actctgtcac ccaggctgga gtgcagtggc    1123 accaccatgg ctctctgcag ccttgacctc tgggagctca agtgatcctc ctgcctcagt   1183 ctcctgagta gctggaacta caaggaaggg ccaccacacc tgactaactt ttttgttttt   1243 tgtttggtaa agatggcatt tcaccatgtt gtacaggctg gtctcaaact cctaggttca   1303 ctttggcctc ccaaagtgct gggattacag acatgaactg ccaggcccgg ccaaaataat   1363 gcaccacttt taacagaaca gacagatgag gacagagctg gtgataaaaa aaaaaaaaa    1423 aaagcatttt ctagatacca cttaacaggt ttgagctagt tttttttgaaa tccaagaaa    1483 attatagttt aaattcaatt acatagtcca gtggtccaac tataattata atcaaaatca   1543 atgcaggttt gttttttggt gctaatatga catatgacaa taagccacga ggtgcagtaa    1603 gtacccgact aaagtttccg tgggttctgt catgtaacac gacatgctcc accgtcaggg   1663 gggagtatga gcagagtgcc tgagtttagg gtcaaggaca aaaaacctca ggcctggagg   1723 aagttttgga aagagttcaa gtgtctgtat atcctatggt cttctccatc ctcacacctt    1783 ctgcctttgt cctgctccct tttaagccag gttacattct aaaaattctt aacttttaac    1843 ataatatttt ataccaaagc caataaatga actgcatatg aaaaaaaaaa aaaaaaaaaa   1903 aaaaaaaaaa aaaaaaaaa aaaaaaaaaa aa                                 1935
```

<210> SEQ ID NO 2

<211> LENGTH: 255
<212> TYPE: PRT
<213> ORGANISM: Homo sapiens

<400> SEQUENCE: 2

Met Gly Asn Ser Cys Tyr Asn Ile Val Ala Thr Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 3
<211> LENGTH: 2350
<212> TYPE: DNA
<213> ORGANISM: Mus musculus
<220> FEATURE:
<221> NAME/KEY: CDS
<222> LOCATION: (146)..(916)
<220> FEATURE:
<221> NAME/KEY: misc_feature
<222> LOCATION: (1253)..(1255)
<223> OTHER INFORMATION: n is a, c, g, or t

<400> SEQUENCE: 3
atgtccatga actgctgagt ggataaacag cacgggatat ctctgtctaa aggaatatta      60
ctacaccagg aaaaggacac attcgacaac aggaaaggag cctgtcacag aaaaccacag     120
tgtcctgtgc atgtgacatt tcgcc atg gga aac aac tgt tac aac gtg gtg      172
                            Met Gly Asn Asn Cys Tyr Asn Val Val
                            1               5 gtc att gtg ctg ctg cta gtg ggc tgt gag aag gtg gga gcc gtg cag      220
Val Ile Val Leu Leu Leu Val Gly Cys Glu Lys Val Gly Ala Val Gln
10                  15                  20                  25

```
aac tcc tgt gat aac tgt cag cct ggt act ttc tgc aga aaa tac aat    268
Asn Ser Cys Asp Asn Cys Gln Pro Gly Thr Phe Cys Arg Lys Tyr Asn
             30                  35                  40 cca gtc tgc aag agc tgc cct cca agt acc ttc tcc agc ata ggt gga    316
Pro Val Cys Lys Ser Cys Pro Pro Ser Thr Phe Ser Ser Ile Gly Gly
             45                  50                  55 cag ccg aac tgt aac atc tgc aga gtg tgt gca ggc tat ttc agg ttc    364
Gln Pro Asn Cys Asn Ile Cys Arg Val Cys Ala Gly Tyr Phe Arg Phe
             60                  65                  70 aag aag ttt tgc tcc tct acc cac aac gcg gag tgt gag tgc att gaa    412
Lys Lys Phe Cys Ser Ser Thr His Asn Ala Glu Cys Glu Cys Ile Glu
 75                  80                  85 gga ttc cat tgc ttg ggg cca cag tgc acc aga tgt gaa aag gac tgc    460
Gly Phe His Cys Leu Gly Pro Gln Cys Thr Arg Cys Glu Lys Asp Cys
 90                  95                 100                 105 agg cct ggc cag gag cta acg aag cag ggt tgc aaa acc tgt agc ttg    508
Arg Pro Gly Gln Glu Leu Thr Lys Gln Gly Cys Lys Thr Cys Ser Leu
                110                 115                 120 gga aca ttt aat gac cag aac ggt act ggc gtc tgt cga ccc tgg acg    556
Gly Thr Phe Asn Asp Gln Asn Gly Thr Gly Val Cys Arg Pro Trp Thr
                125                 130                 135 aac tgc tct cta gac gga agg tct gtg ctt aag acc ggg acc acg gag    604
Asn Cys Ser Leu Asp Gly Arg Ser Val Leu Lys Thr Gly Thr Thr Glu
            140                 145                 150 aag gac gtg gtg tgt gga ccc cct gtg gtg agc ttc tct ccc agt acc    652
Lys Asp Val Val Cys Gly Pro Pro Val Val Ser Phe Ser Pro Ser Thr
155                 160                 165 acc att tct gtg act cca gag gga gga cca gga ggg cac tcc ttg cag    700
Thr Ile Ser Val Thr Pro Glu Gly Gly Pro Gly Gly His Ser Leu Gln
170                 175                 180                 185 gtc ctt acc ttg ttc ctg gcg ctg aca tcg gct ttg ctg ctg gcc ctg    748
Val Leu Thr Leu Phe Leu Ala Leu Thr Ser Ala Leu Leu Leu Ala Leu
                190                 195                 200 atc ttc att act ctc ctg ttc tct gtg ctc aaa tgg atc agg aaa aaa    796
Ile Phe Ile Thr Leu Leu Phe Ser Val Leu Lys Trp Ile Arg Lys Lys
                205                 210                 215 ttc ccc cac ata ttc aag caa cca ttt aag aag acc act gga gca gct    844
Phe Pro His Ile Phe Lys Gln Pro Phe Lys Lys Thr Thr Gly Ala Ala
                220                 225                 230 caa gag gaa gat gct tgt agc tgc cga tgt cca cag gaa gaa gaa gga    892
Gln Glu Glu Asp Ala Cys Ser Cys Arg Cys Pro Gln Glu Glu Glu Gly
235                 240                 245 gga gga gga ggc tat gag ctg tga tgtactatcc taggagatgt gtgggccgaa   946
Gly Gly Gly Gly Tyr Glu Leu
250                 255 accgagaagc actaggaccc caccatcctg tggaacagca caagcaaccc caccaccctg  1006
ttcttacaca tcatcctaga tgatgtgtgg gcgcgcacct catccaagtc tcttctaacg  1066
ctaacatatt tgtctttacc tttttttaaat cttttttttaa atttaaattt tatgtgtgtg  1126
agtgttttgc ctgcctgtat gcacacgtgt gtgtgtgtgt gtgtgtgaca ctcctgatgc  1186
ctgaggaggt cagaagagaa agggttggtt ccataagaac tggagttatg gatggctgtg  1246
agccggnnng ataggtcggg acggagacct gtcttcttat tttaacgtga ctgtataata  1306
aaaaaaaaat gatatttcgg gaattgtaga gattctcctg acacccttct agttaatgat  1366
ctaagaggaa ttgttgatac gtagtatact gtatatgtgt atgtatatgt atatgtatat  1426
ataagactct tttactgtca aagtcaacct agagtgtctg gttaccaggt caatttttatt  1486 ggacatttta cgtcacacac acacacacac acacacacac acgtttatac tacgtactgt  1546
```

```
tatcggtatt ctacgtcata taatgggata gggtaaaagg aaaccaaaga gtgagtgata   1606
ttattgtgga ggtgacagac taccccttct gggtacgtag ggacagacct ccttcggact   1666
gtctaaaact ccccttagaa gtctcgtcaa gttcccggac gaagaggaca gaggagacac   1726

agtccgaaaa gttatttttc cggcaaatcc tttccctgtt tcgtgacact ccaccccttg   1786
tggacacttg agtgtcatcc ttgcgccgga aggtcaggtg gtacccgtct gtaggggcgg   1846
ggagacagag ccgcggggga gctacgagaa tcgactcaca gggcgccccg ggcttcgcaa   1906
atgaaacttt tttaatctca caagtttcgt ccgggctcgg cggacctatg gcgtcgatcc   1966
ttattacctt atcctggcgc caagataaaa caaccaaaag ccttgactcc ggtactaatt   2026
ctccctgccg gcccccgtaa gcataacgcg gcgatctcca ctttaagaac ctggccgcgt   2086
tctgcctggt ctcgctttcg taaacggttc ttacaaaagt aattagttct tgctttcagc   2146
ctccaagctt ctgctagtct atggcagcat caaggctggt atttgctacg gctgaccgct   2206
acgccgccgc aataagggta ctgggcggcc cgtcgaaggc cctttggttt cagaaaccca   2266
aggccccccct cataccaacg tttcgacttt gattcttgcc ggtacgtggt ggtgggtgcc   2326
ttagctcttt ctcgatagtt agac                                           2350
```

<210> SEQ ID NO 4
<211> LENGTH: 256
<212> TYPE: PRT
<213> ORGANISM: Mus musculus

<400> SEQUENCE: 4

```
Met Gly Asn Asn Cys Tyr Asn Val Val Val Ile Val Leu Leu Leu Val
1               5                   10                  15

Gly Cys Glu Lys Val Gly Ala Val Gln Asn Ser Cys Asp Asn Cys Gln
            20                  25                  30

Pro Gly Thr Phe Cys Arg Lys Tyr Asn Pro Val Cys Lys Ser Cys Pro
        35                  40                  45

Pro Ser Thr Phe Ser Ser Ile Gly Gly Gln Pro Asn Cys Asn Ile Cys
    50                  55                  60

Arg Val Cys Ala Gly Tyr Phe Arg Phe Lys Lys Phe Cys Ser Ser Thr
65                  70                  75                  80

His Asn Ala Glu Cys Glu Cys Ile Glu Gly Phe His Cys Leu Gly Pro
                85                  90                  95

Gln Cys Thr Arg Cys Glu Lys Asp Cys Arg Pro Gly Gln Glu Leu Thr
            100                 105                 110

Lys Gln Gly Cys Lys Thr Cys Ser Leu Gly Thr Phe Asn Asp Gln Asn
        115                 120                 125

Gly Thr Gly Val Cys Arg Pro Trp Thr Asn Cys Ser Leu Asp Gly Arg
    130                 135                 140

Ser Val Leu Lys Thr Gly Thr Thr Glu Lys Asp Val Val Cys Gly Pro
145                 150                 155                 160

Pro Val Val Ser Phe Ser Pro Ser Thr Thr Ile Ser Val Thr Pro Glu
                165                 170                 175

Gly Gly Pro Gly Gly His Ser Leu Gln Val Leu Thr Leu Phe Leu Ala
            180                 185                 190

Leu Thr Ser Ala Leu Leu Leu Ala Leu Ile Phe Ile Thr Leu Leu Phe
        195                 200                 205
```

```
Ser Val Leu Lys Trp Ile Arg Lys Lys Phe Pro His Ile Phe Lys Gln
    210             215             220
Pro Phe Lys Lys Thr Thr Gly Ala Ala Gln Glu Glu Asp Ala Cys Ser
225             230             235             240
Cys Arg Cys Pro Gln Glu Glu Glu Gly Gly Gly Gly Tyr Glu Leu
            245             250             255
```